(12) United States Patent
Strauss et al.

(10) Patent No.: US 7,871,566 B2
(45) Date of Patent: Jan. 18, 2011

(54) DEVICE FOR ENRICHING AND/OR DEPLETING MATERIALS IN A LIQUID

(75) Inventors: Andreas Strauss, Aachen (DE); Mustafa Akdis, Merenberg (DE)

(73) Assignee: Ilias-medical GmbH, Koln (DE)

( * ) Notice: Subject to any disclaimer, the term of this patent is extended or adjusted under 35 U.S.C. 154(b) by 420 days.

(21) Appl. No.: 12/064,030

(22) PCT Filed: Aug. 18, 2006

(86) PCT No.: PCT/EP2006/008178
§ 371 (c)(1),
(2), (4) Date: Jun. 12, 2008

(87) PCT Pub. No.: WO2007/020106
PCT Pub. Date: Feb. 22, 2007

(65) Prior Publication Data
US 2008/0234623 A1 Sep. 25, 2008

(30) Foreign Application Priority Data
Aug. 18, 2005 (DE) ........................ 10 2005 039 446

(51) Int. Cl.
*A61M 37/00* (2006.01)
*A61M 1/00* (2006.01)
*B01D 33/21* (2006.01)

(52) U.S. Cl. .......................... 422/45; 422/44; 604/4.01; 604/6.14; 210/500.23

(58) Field of Classification Search ................ 604/4.01, 604/5.01, 6.14, 6.11; 422/44, 45; 210/203, 210/321.78, 321.79, 321.88, 500.23
See application file for complete search history.

(56) References Cited

U.S. PATENT DOCUMENTS 5,266,265 A 11/1993 Raible (Continued)

FOREIGN PATENT DOCUMENTS

DE 2251176 4/1974

(Continued)

OTHER PUBLICATIONS

PCT International Preliminary Report on Patentability, International Application No. PCT/EP2006/008178, International Filing Date Aug. 18, 2006, Translation.

(Continued)

*Primary Examiner*—Leslie R Deak
(74) *Attorney, Agent, or Firm*—International IP Law Group, P.C.

(57) ABSTRACT

A device and method for enriching and/or depleting substances in a liquid is disclosed. An exemplary device comprises a membrane module that consists essentially of concentric elements and that has a separation element in which the substance to be enriched and/or depleted is carried, and whereby the liquid is carried outside of the separation element. The exemplary device also comprises a drive module that encompasses a drive unit for driving a conveying element that conveys the liquid, the drive unit having a radial magnetic coupling for a central impeller located on the inside. The exemplary device further comprises a conveying module for conveying the liquid through the device, housing the conveying element, whereby the drive module is adapted to be inserted into and removed from the membrane module with a liquid-tight closure. The exemplary device further an oxygenator having an outside fiber bundle and an inside fiber bundle. Finally, the exemplary device comprises an electromagnetic drive unit disposed between the outside fiber bundle and the inside fiber bundle.

40 Claims, 18 Drawing Sheets

U.S. PATENT DOCUMENTS

| | | |
|---|---|---|
| 5,270,005 A | 12/1993 | Raible |
| 5,308,314 A | 5/1994 | Fukui et al. |
| 5,676,526 A | 10/1997 | Kuwana et al. |
| 5,817,279 A | 10/1998 | Eilers et al. |
| 5,840,070 A | 11/1998 | Wampler |
| 6,071,093 A | 6/2000 | Hart |
| 6,116,862 A | 9/2000 | Rau et al. |
| 2004/0223872 A1 | 11/2004 | Brian et al. |

FOREIGN PATENT DOCUMENTS

| | | |
|---|---|---|
| DE | 3831457 | 3/1990 |
| DE | 3923692 | 1/1991 |
| DE | 69317763 | 4/1994 |
| DE | 4238884 | 5/1994 |
| DE | 69431792 | 2/1995 |
| DE | 10108810 | 8/2002 |
| DE | 10341221 | 3/2005 |
| EP | 0507722 | 10/1992 |
| EP | 0611580 | 8/1994 |
| EP | 0765683 | 4/1997 |
| EP | 0625057 | 4/1998 |
| EP | 0895786 | 2/1999 |
| JP | 02041172 | 2/1990 |
| WO | WO9504558 | 2/1995 |
| WO | WO9716213 | 9/1997 |

OTHER PUBLICATIONS

PCT International Preliminary Report on Patentability, Nov. 22, 2007 (Not translated).

DEVICE FOR ENRICHING AND/OR DEPLETING MATERIALS IN A LIQUID

CROSS REFERENCE TO RELATED APPLICATIONS

Pursuant to 35 U.S.C. §371, this application is the United States National Stage Application of International Patent Application No. PCT/EP2006/008178, filed on Aug. 18, 2006, the contents of which are incorporated by reference as if set forth in their entirety herein, which claims priority to German (DE) Patent Application No. 102005039446.9, filed Aug. 18, 2005, the contents of which are incorporated by reference as if set forth in their entirety herein.

BACKGROUND

The invention relates to a device and to a method for enriching and/or depleting substances in blood.

German specification DE 42 38 884 discloses a system consisting of the following individual components: oxygenator, heat exchanger, blood filter and blood reservoir, all of which are connected to each other via tubes for transporting the blood.

By the same token, membrane oxygenators with integrated membrane elements and an integrated heat exchanger, whereby the heat exchanger element is firmly affixed in the oxygenator, can be found in the state of the art, as disclosed in Europe specification EP 0507722.

Another embodiment of an oxygenator is disclosed in German specification DE 69317763. This document describes a modularly structured, integrated disposable blood oxygenator having a replaceable heat exchanger element.

A device for treating liquids, especially blood, disclosed in European specification EP 0765683 and in U.S. Pat. No. 5,817,279, consists, for example, of several chambers that are made up of tubes. A compact structure is achieved, among other things, in that a cyclone is arranged partially in a tube.

Numerous centrifugal pumps that serve to convey blood are likewise known from the state of the art.

For instance, German patent application DE 101 08 810 A1 shows a blood pump in which the impeller is supported contact-free by electronically regulated magnetic bearings. Aside from the drive energy, additional energy is needed for the contact-free bearing of the rotor.

U.S. Pat. No. 5,840,070 discloses a pump in which the rotor is supported by a plurality of magnets accommodated in the impeller as well as in the pump housing.

Furthermore, U.S. Pat. No. 6,116,862 discloses a blood pump with an impeller wheel that, for purposes of stabilizing the rotor, uses two mechanical sliding bearings that are subject to wear and tear. One of these rotor bearings contains a universal ball joint bearing on the rear of the impeller wheel for purposes of axial rotor stabilization. Especially the attractive forces from the magnetic coupling device are absorbed by the first bearing. The second rotor bearing contains a shaft-bush bearing for radially stabilizing the rotor as well as for absorbing tilting forces resulting from the magnetic coupling.

SUMMARY OF THE INVENTION

An exemplary embodiment of the present invention is based on the objective of putting forward a mobile, compact, extracorporeal oxygenation system that has the smallest possible filling volume and whose surface area that comes into contact with the outside is minimized. Besides, this system should be easy to handle, fast to deploy, gentle on the blood and re-usable.

According to an exemplary embodiment of the present invention, a device for enriching and depleting substances in a liquid is provided with a membrane module that consists essentially of concentric elements and that has a separation element for enriching and depleting a liquid, whereby the substance to be depleted and enriched is carried inside the separation element while the liquid is carried outside of the separation element.

In a practical manner, an especially preferred embodiment of the invention comprises a compact, mobile oxygenation system having a low filling volume, a minimized membrane surface area as well as an integrated, fluid-mechanically mounted, replaceable and optionally re-useable blood pump as well as an optimized gas feed for the intracorporeal or extracorporeal oxygenation of patients.

The device is replaceable, even while it is connected to at least one blood vessel of a patient. This means that, when the drive unit is replaced, the operation of the device is interrupted for only a very brief period of time, for example, between 1 second and 30 seconds, preferably 20 seconds at the maximum. In terms of the physiological effect, this means that the device can be replaced during operation.

The device comprises a drive module that encompasses a drive unit for driving a conveying element that conveys the liquid.

In a particularly preferred embodiment of the device, the conveying element is a rotor.

The device is characterized in that the drive module can be inserted into and removed from the membrane module with a liquid-tight closure.

As a result, the drive module can be inserted into and removed from the membrane module during operation.

It is practical to arrange the conveying module for conveying the liquid in the axial extension of the drive module.

This has the advantage that it is easier to separate the drive module from the conveying module.

Moreover, it is practical to arrange the conveying element and a housing that surrounds it, preferably a rotor housing, in such a way that they can be separated from each other.

In this case, the conveying element—preferably a rotor—remains in the liquid while the drive module is being replaced.

The conveying element is also replaceable if the conveying element—preferably a rotor—is sealed so as to be liquid-tight relative to feed lines for the liquid and/or to discharge lines for the liquid.

The liquid can be warmed up, thanks to the fact that the drive unit is arranged in the liquid.

This liquid is preferably not in direct contact with the drive unit, but rather, is separated from it by means of an additional partition.

The elements can be any desired geometrical structures, provided that they can be arranged concentrically. In order to reduce the space requirements, preference is given to a design having radially symmetrical shapes, especially in the form of spheres, ellipsoids or cylinders.

It is practical to configure the separation element in such a way that it has hollow fibers made of semi-permeable material for purposes of enriching and/or depleting the liquid.

The use of hollow fibers made of semi-permeable material is advantageous. These fibers allow particularly efficient separation processes by means of diffusion.

A preferred embodiment of the invention puts forward the use of at least one semi-permeable membrane. The term "semi-permeable" here refers to a configuration of the membrane in which a first substance, preferably oxygen and/or $CO_2$, is allowed to pass through while another substance, preferably water, is prevented from doing so.

It is likewise advantageous for the separation element to be provided with a semi-permeable material for purposes of enriching and/or depleting a liquid.

Preferably, the semi-permeable material contains fiber membranes, whereby the substance to be depleted is arranged between the fibers, and the substance to be enriched is arranged in the hollow fibers.

This increases the surface area available for the separation effect.

The slanted arrangement of fibers creates turbulences in the liquid, especially in the blood. As a result, the mass transfer and thus the separation effect are enhanced.

In order to improve the replaceability, it is practical for the drive module to have a quick-release closure on at least one of its ends.

Preferably, the quick-release closure is located on the base element of the oxygenation system.

In order to ensure reliable latching and to prevent accidental opening, in a special embodiment, the quick-release closure can be a bayonet coupling.

Other examples of suitable quick-release closures are screw closures and clamp-type closures.

Magnetic closures are also practical.

The closure is preferably arranged at one end of the element. As a result, the drive element can be securely affixed during the operation of the device.

Preferably, the drive element is a motor or a turbine. The term motor encompasses all drives that are suitable to transfer a torque to the conveying element. The use of an electric motor is particularly preferred. The turbine is preferably driven pneumatically.

Advantageously, a shock-absorbing element is arranged between the drive unit and a rotor unit.

The shock-absorbing element is advantageously configured in such a way that it reduces impacts when the drive element is being inserted.

Preferably, the shock-absorbing element consists of a cavity filled with air that is connected to one or more small escape openings for the air.

Here, the outlet openings for the air are dimensioned in such a way that the insertion of the drive element is delayed by at least 0.5 seconds, preferably between 1 second and 10 seconds.

In the case of especially preferred volumes of air to be displaced, particularly between about 10 ml and about 500 ml, preferably 200 ml at the maximum, the flow of outgoing air to be established in order to achieve the desired delay lies between 1 ml/s and 500 ml/s. In the case of especially advantageous air volumes between 10 ml and 200 ml and of a desired minimum delay between 2 seconds and 10 seconds, the flow of outgoing air to be established lies between 5 ml/s and 100 ml/s.

The invention has several advantages over the ECMO systems currently known.

Especially preferred embodiments of the invention are characterized by the following: owing to the ease of handling and the low weight of the system, it can be used not only in stationary situations but it can also be transported as a mobile unit directly to the site of accidents in ambulances, emergency physician vehicles or helicopters. The device can be easily carried and operated by one person and, thanks to its compact design, can fit in medical bags.

The preferred breakdown into a re-useable blood pump drive module—the drive unit—and into a disposable unit—a module that surrounds the drive unit, preferably a membrane module—allows the versatile use of the device according to the invention.

If the blood pump is integrated directly into the oxygenator, it contributes at the same time to the temperature control of the blood.

This dispenses with the need for an external heat exchanger aggregate. It is nevertheless likewise possible to use such a heat exchanger aggregate to further warm up the blood, whereby, however, embodiments without the additional heat exchanger aggregate are more advantageous since they are more compact. No tube connections and connectors are needed in order to connect the components to each other. The enhances the safety and additionally reduces the surface area that comes into contact with the outside as well as the filling volume (that is to say, the volume with which the system has to be filled with foreign blood or blood substitute liquid in order to displace the air from the system, thus preventing embolisms). The drive of the integrated blood pump can be removed quickly and easily—even during operation—and it can be re-used since it does not come into contact with blood. Owing to the small filling volume, the invention is also particularly well-suited for use in children as well.

Furthermore, it is practical to employ at least one sensor. Especially practical examples are sensors for measuring the temperature of the blood, the flow rate of the blood and/or the blood gases.

Moreover, it is practical to use at least one pressure sensor. The use of a pressure sensor allows an equalization between an actual pressure and predefinable target pressures.

It is particularly advantageous to use at least one sensor in the vicinity of an element or inside one of the elements. Moreover, it is advantageous to arrange at least one sensor in the vicinity of a cover.

The membrane module of the invention has at least two elements.

The elements are, for instance, cylinders arranged concentrically with respect to each other, whereby:

hollow, microporous membranes are placed between the cylinders, and the spaces between the cylinders are sealed off at the ends so as to be liquid-tight;

the innermost of the three cylinders has a cover with a quick-release closure on the side opposite from the conveying module.

In order to reduce filling volume while taking safety aspects into consideration, a practical embodiment of the conveying module is configured geometrically in such a way that it can be placed inside the interior of the innermost of the at least two elements and can be inserted into and it removed from it during operation.

A particularly preferred embodiment of the conveying module is configured in such a manner that its radial outer diameter is smaller than the radius of the interior of the innermost cylinder.

A practical embodiment of the conveying module is characterized in that it can be inserted into the interior of the innermost cylinder during the assembly of the device.

In order to allow the connection of a double-lumen catheter, it is advantageous to place a cap onto one of the ends of one of the cylinders according to the invention, said cap having a feed line and a discharge line arranged coaxially to each other for feeding and discharging the liquid.

For purposes of optimizing the gas transport, especially for eliminating the $CO_2$, it is practical for each of the microporous membranes that are placed between the first and the second elements and/or between the second and a third element to be provided with a substance feed line and a substance discharge line.

Such embodiments are particularly advantageous when the elements are rotation-symmetrical, especially spheres, ellipsoids or cylinders.

For this reason, in a preferred embodiment, the gas feed lines of the membranes placed between the first and the second elements and/or the membranes placed between the second and the third elements are arranged at opposite ends of the cylinders.

In order to minimize trauma to the blood and thrombogenesis as well as to ensure the modularity, it is practical for the device for enriching and/or depleting substances in a liquid to be configured with a drive unit to drive a conveying element that conveys the liquid in such a way that it transfers the force and/or the torque of the drive unit to the conveying element contact-free.

In a particularly preferred embodiment, this is achieved in that the device for enriching and/or depleting substances in a liquid is configured with a drive unit to drive a conveying element that conveys the liquid in such a way that it transfers the force and/or the torque of the drive unit to the conveying element by means of a magnetic coupling.

A practical embodiment of the device proposes accommodating a drive unit in an essentially cylindrical receptacle, said drive unit generating heat during operation.

A practical embodiment of the device proposes accommodating a drive unit in an essentially cylindrical receptacle, said drive unit being an electric motor.

A practical embodiment of the device proposes accommodating a drive unit in an essentially cylindrical receptacle, said drive unit being a turbine.

A practical embodiment of the invention proposes accommodating a drive unit in an essentially cylindrical receptacle, said drive unit being in heat-conducting contact with a cylindrical receptacle along whose outside liquid is carried.

It is advantageous for the device to have a conveying element that is fitted in the radial direction with a fluid-mechanical bearing and/or with a magnetic bearing that is effectuated by a secondary flow that runs counter to the main conveying flow in a space between the conveying element and the surrounding housing.

An advantage of such a bearing is the simple structure and design of the fluid bearing. In a particularly preferred embodiment, the fluid bearing is configured in such a way that the conveying element with its bearing clearances (approximately 100 µm to 1000 µm), in comparison to conventional hydrodynamic bearings (approximately 10 µm to 100 µm), can be operated even at larger bearing clearances. This especially entails the advantage that, in the present invention, the damage to the blood cells is considerably less than with conventional hydrodynamic bearings, so that the oxygenation system described in the present invention can be operated in a much more patient-friendly manner.

It is advantageous for the device to have a conveying element that is mounted in a solid axial bearing in the side facing the drive module.

An especially preferred embodiment of the device encompasses an oxygenator. It is also possible for the device itself to be an oxygenator.

It is advantageous to configure the device in such a way that, in its interior, it surrounds a blood pump that is fluid-mechanically stabilized in the radial direction.

An especially preferred embodiment of the device is characterized in that it has an axial, radial or diagonal centrifugal blood pump.

It is practical to configure an oxygenator according to the invention in such a manner that it has an outside fiber bundle and an inside fiber bundle, whereby an electromagnetic drive unit is integrated between the outside fiber bundle and the inside fiber bundle, said drive unit having a radial magnetic coupling for a central impeller located on the inside.

It is also advantageous for the oxygenator to have an outside fiber bundle and an inside fiber bundle, whereby an electromagnetic drive unit is integrated between the outside fiber bundle and the inside fiber bundle, said drive unit creating a radial magnetic coupling for the central impeller located on the inside.

An especially preferred embodiment of the device is characterized in that the magnetic forces that act in the magnetic coupling stabilize the impeller in the pump housing.

It is also practical to configure an oxygenator according to the invention in such a way that it has an outside fiber bundle and an inside fiber bundle, whereby an electromagnetic drive unit is integrated between the outside fiber bundle and the inside fiber bundle, said drive unit warming up the outside fiber bundle as well as the inside fiber bundle.

It is advantageous to configure a device according to the invention with at least two drive modules.

An arrangement of two serially connected drive modules allows the use of smaller and more compact drive modules.

It is particularly advantageous to arrange two drive modules so as to be connected in parallel. In this case, while one of the drive modules is out of operation, the other drive module can continue to be operated. Moreover, it is possible to replace one drive module while the other drive module delivers the desired drive power.

DETAILED DESCRIPTION OF SPECIFIC EMBODIMENTS

The invention will explained in greater detail below on the basis of exemplary embodiments.

In a practical manner, the device has means that allow fluids to be fed into and discharged from the system. These means are, for instance, an inlet channel and an outlet channel. However, several inlet channels and/or outlet channels can also be provided.

The blood flows into the oxygenator through a blood inlet and is first carried through an integrated blood pump. Subsequently, the blood flows into a chamber, and from there, it flows out of the system via a blood outlet.

The blood inlet and the blood outlet of the oxygenation system can be configured coaxially, so that a double-lumen catheter can be connected directly—without an adapter. This has the advantage that overlapping in the tube system is avoided. As a result, flow separations, dead water zones or thrombus formation are prevented. This also shortens the time needed until the oxygenation system is ready for use.

This is a decisive advantage, particularly during critical situations.

Figure 1:
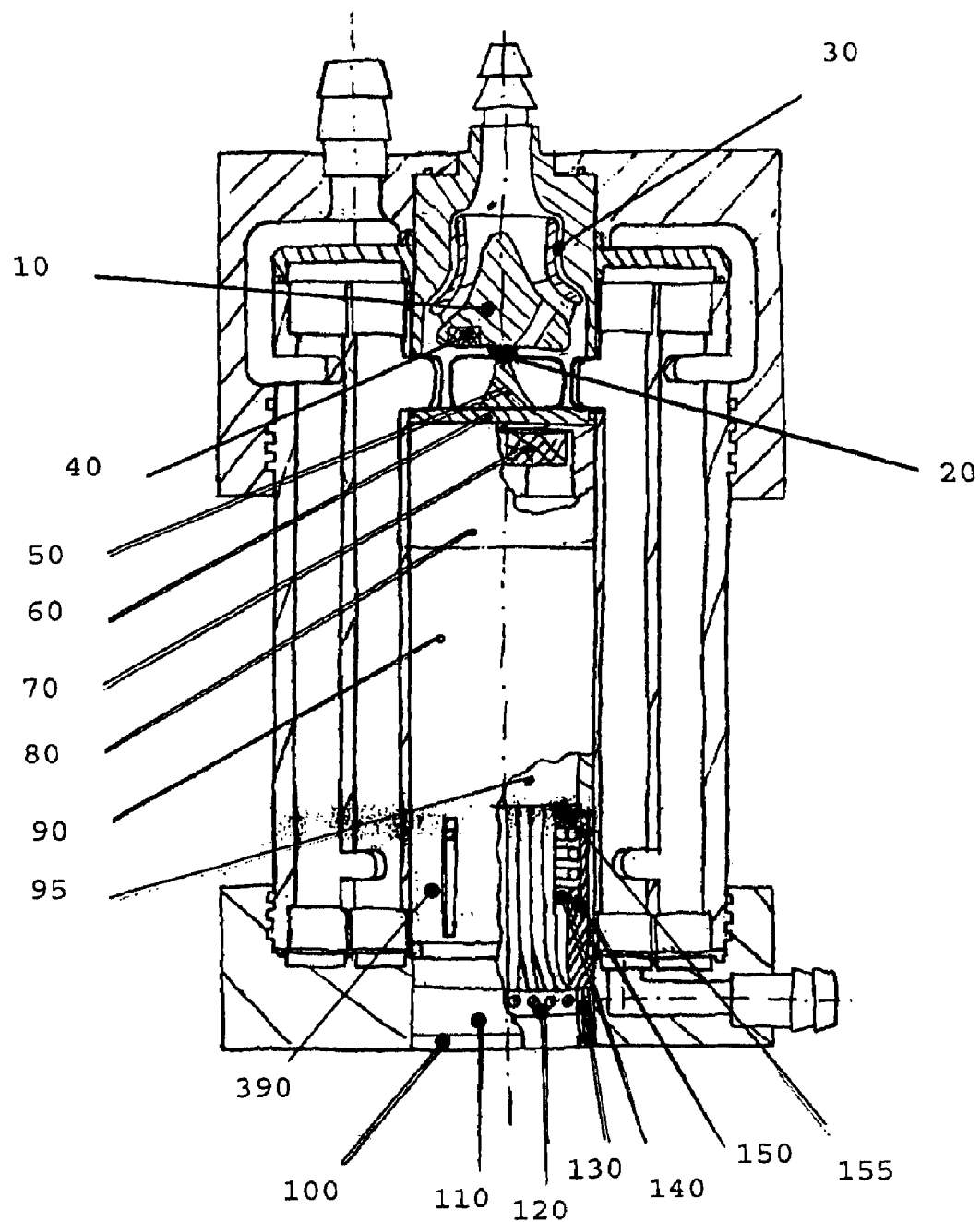
FIG. 1 is a cross-sectional view of an oxygenation system according to an exemplary embodiment of the present invention, showing a flow bearing of a blood pump and showing a quick-release closure.

FIG. 1 shows a section through the oxygenation system that is essentially rotation-symmetrical around its longitudinal axis, with an integrated blood pump. The system consists essentially of an oxygenator and a blood pump that is placed therein. The oxygenator consists of a membrane module made up of the cylinders 250, 260 and 270, as well as of the fibers 330 and 340 contained therein, and of the cover elements 230 and 240 on the ends. The blood pump is made up of the conveying modules 10-60 and drive modules 70-150. For purposes of the assembly, the conveying module is inserted into the innermost cylinder 250 of the oxygenator.

The conveying module is affixed by the shoulder formations on the opening of the cover 230 and by the nut 170. The drive module has a quick-release closure that, in the present case, is configured as a bayonet coupling consisting of a pushbutton 100, a connector holder 110 that affixes the connector 120, a ring element 130, a spring 140 and the return pins 150. When the unit is inserted into the oxygenation system, the coupling latches into the grooves 400 provided for this purpose in the cover 240. The spring presses the drive module against the rotor module, thus axially affixing the drive module. Depressing the button while turning the bayonet coupling causes it to unlatch once again. The spring causes the pushbutton 100 to pop out of the oxygenator housing, so that the drive unit can be easily and quickly removed from the oxygenator.

The impeller 10 is driven by the motor 90 by means of a magnetic coupling 40, 70. The support bearing 20, which absorbs the attractive forces from the magnetic coupling 40, 70, serves as the axial bearing of the impeller 10. The radial stabilization of the impeller 10 is effectuated contact-free by means of the fluid-mechanical bearing 30, which absorbs the tilting forces from the magnetic coupling 40, 70.

Figure 2:
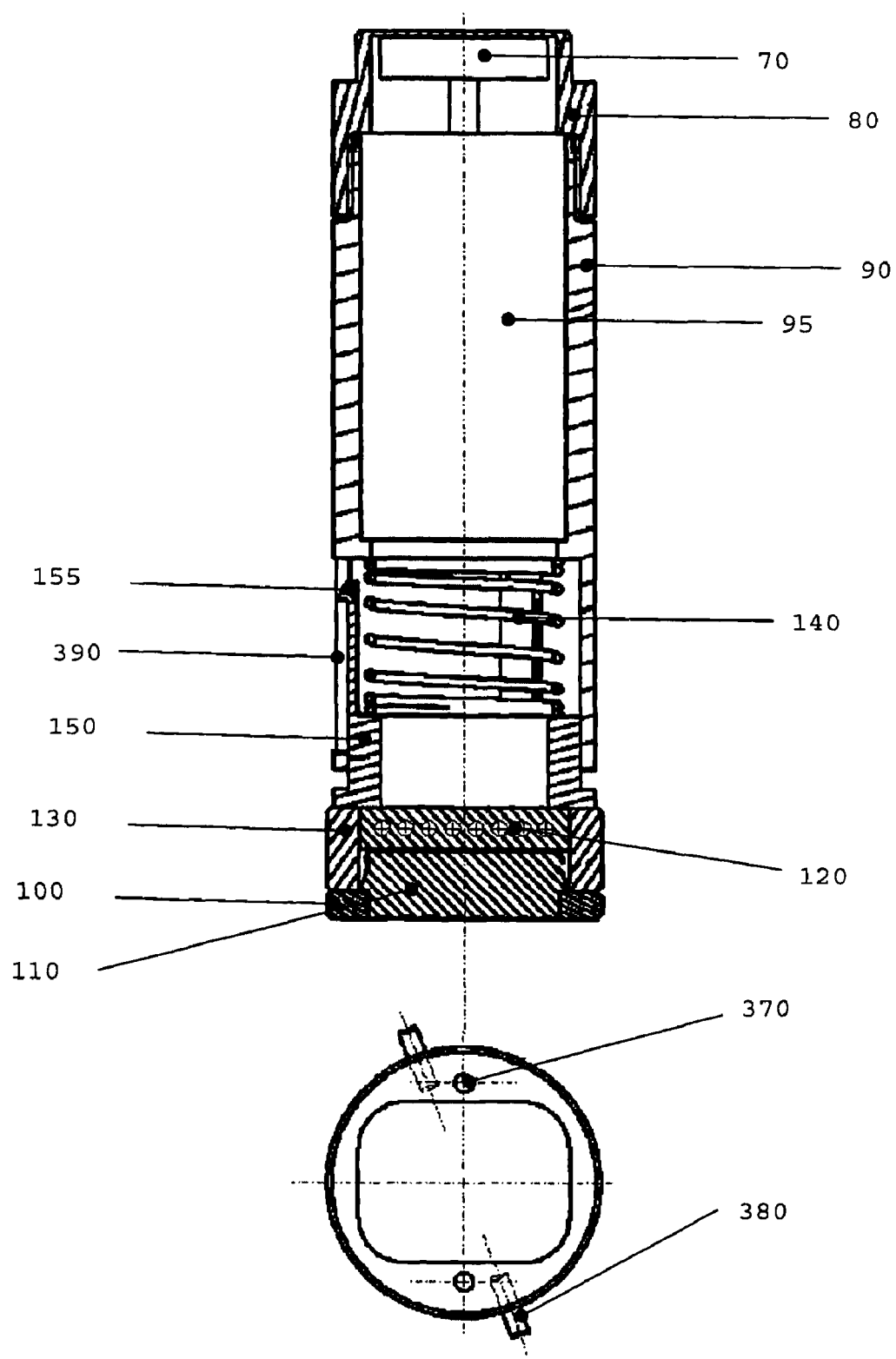
FIG. 2 is a longitudinal cross-sectional view of a drive module with a quick-release closure.

FIG. 2 shows the drive module, consisting of a motor 95 with a magnetic coupling 70, an eight-pole cable and a connector 120. The motor with the magnetic coupling is completely surrounded by the motor housing 90 when the motor cover 80 is screwed on. The cable with the connector leads out of the housing. The connector is affixed in a multi-part device 100-150 by two screws 370 in such a way that a direct connection to the mating connector of the power supply is possible from the outside. The middle component of the three-part connector holder is a ring 130 having two bores into which two alignment pins 380 for the bayonet joint are inserted. The largest component of the connector holder 150 is fitted with three hooks 150 on the side facing away from the connector. These hooks 150 engage with the slits 390 in the motor housing, thus holding the drive module together, but nevertheless allowing an axial movement relative to the motor housing 90. In the installed state, the spring 140 in the interior of the drive module ensures a play-free axial positioning of the motor housing 90 in the cylinder 250. When the bayonet joint is released, the spring pushes the connector and the holder out of the inner cylinder 250, while the other components of the drive module—at first unchanged—are held in the oxygenation unit by the attractive force of the magnetic coupling. The person operating the system can now grasp the connector holder and remove the drive module from the oxygenator. The motor has double protection against rotation due to the motor torque. The torque is directly absorbed by the motor housing into which the motor is clamped by the motor cover. The motor housing, in turn, is secured by the bayonet joint against turning, the torque is absorbed by the element pair consisting of the groove and pin.

Figure 3:
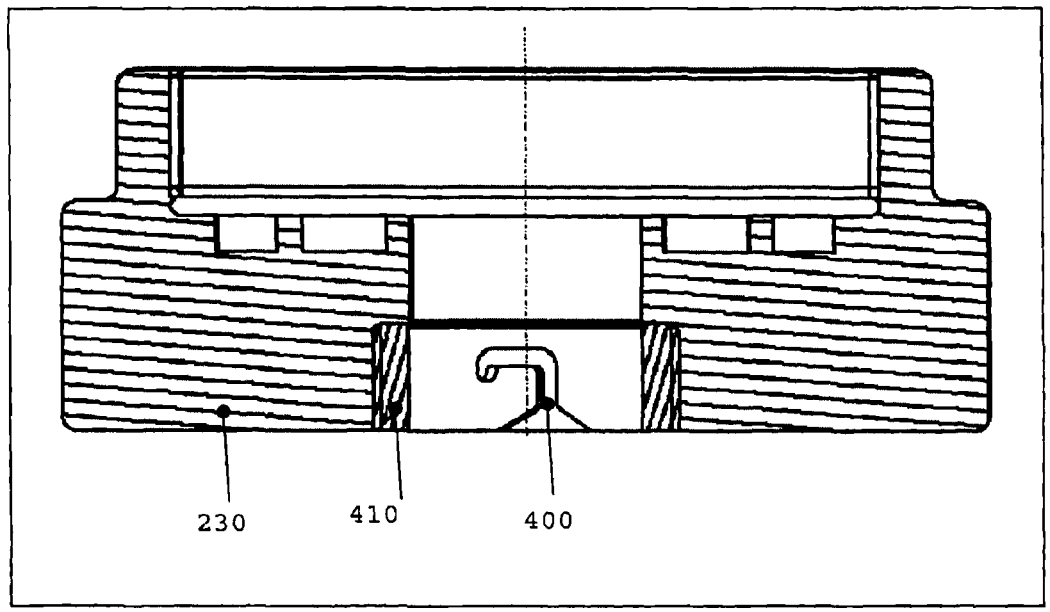
FIG. 3 is a cross-sectional view of a cover with a recess and grooves in accordance with an exemplary embodiment of the present invention.

FIG. 3 shows a cover on the connector side made up of two parts: a bayonet groove 400 is provided in a separate cylinder 410, which considerably simplifies the production. The cylinder is connected to the cover 230 by means of a thread.

Figure 4:
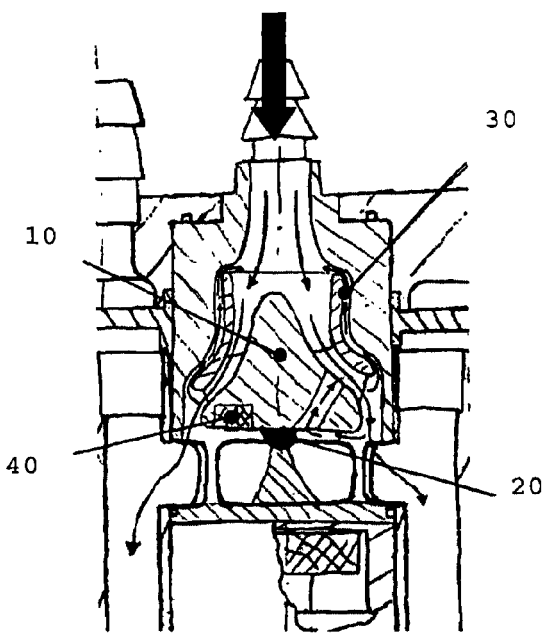
FIG. 4 is a cross-sectional view of a section of a flow bearing in accordance with an exemplary embodiment of the present invention.

FIG. 4 shows the flow guidance in the area of the impeller as well as in the fluid-mechanical bearing 30. The flow conveyed by the impeller 10 is then fed primarily into the flow channel between the first cylinder 250 and the second cylinder 260. After leaving the impeller 10, part of this flow is branched off into the ring channel between the impeller 10 and the surrounding housing. This reversely oriented flow brings about a radial stabilization of the impeller 10.

Figure 5:
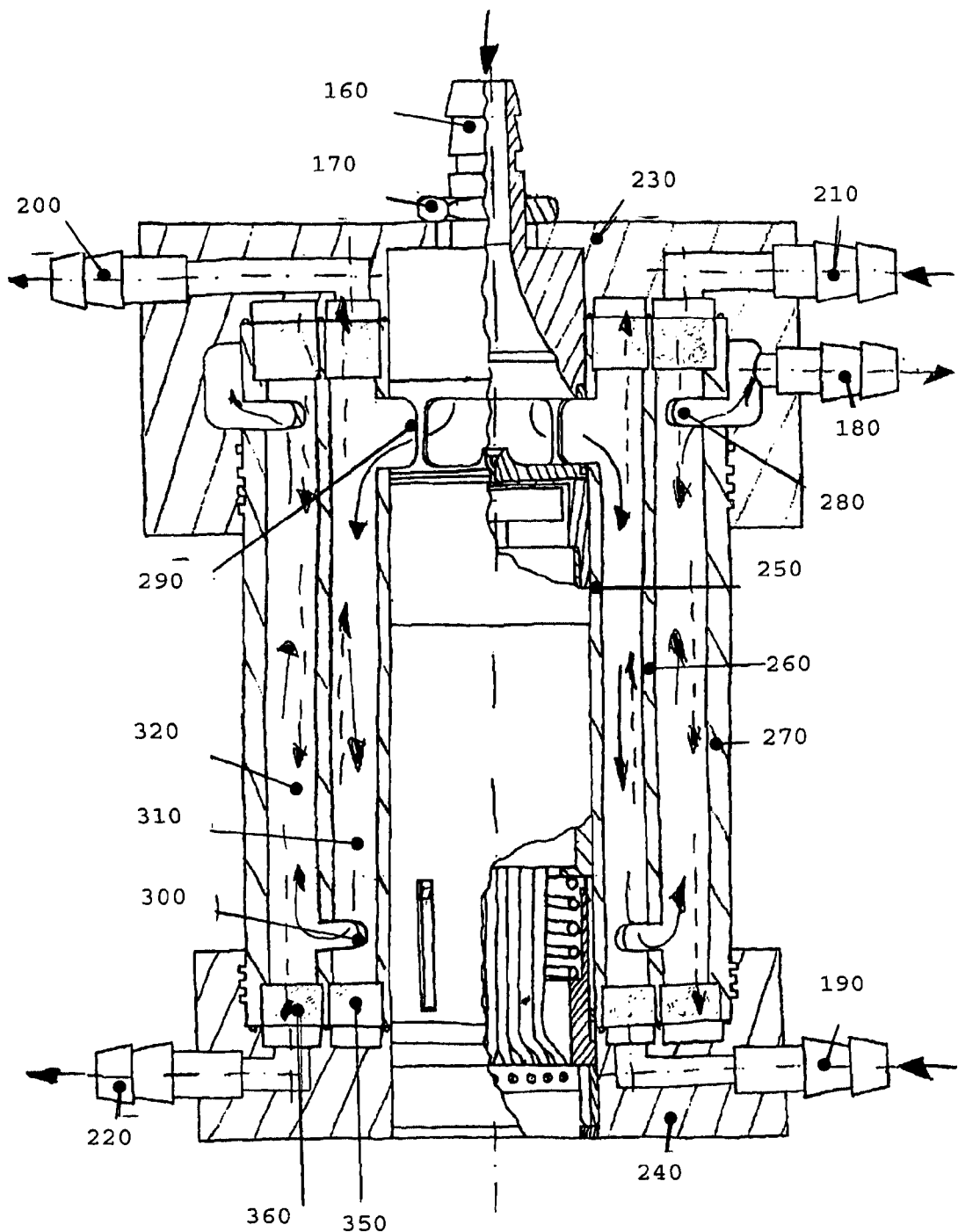
FIG. 5 is a cross-sectional view through an oxygenation system with lines indicating the blood flow course and the flow course of the gas flow that is fed in a double countercurrent.

FIG. 5 shows how the blood flow (solid lines) and the gas flow (broken lines) are carried twice in a countercurrent with respect to each other. The blood flows through the inlet 160 into the oxygenator. There, it flows—as indicated by the arrows—first through the opening 290 in the first cylinder 250 into the first chamber 310 that is closed at its ends by the glued bond 350, where it then flows past the semi-permeable hollow fiber membranes 330. Subsequently, after the blood has passed the recesses 300 in the second cylinder 260, it flows in the opposite direction in the second chamber 320 that is likewise glued at its ends. The blood flows into the blood cover 230 via the passages 280 in the third cylinder 270 and leaves the system through the blood outlet 180. The double countercurrent oxygenation is made possible in that oxygen first enters the system through the gas inlet 190 and subsequently flows into the chamber 310 through the membranes that are arranged between the first cylinder 250 and the second cylinder 260. This gas flow leaves the oxygenation system through the outlet 200. A second gas flow 210 is concurrently carried through the membranes into the chamber 320, between the second cylinder 260 and the third cylinder 270, and then flows out again through the second gas outlet 220.

The feed of fresh oxygen several times ensures an effective gas transfer. In particular, this preferred embodiment of the invention promotes the transfer of carbon dioxide, whose elimination is very important. In the embodiment shown, oxygen or an air mixture is fed into the system in a countercurrent at two places. Additional advantages of this arrangement are the more flexible metering, control and regulation of the gas feed. Therefore, depending on the clinical picture, first of all, pure oxygen can be fed into the first chamber and then a defined air mixture can be fed into the second chamber, for example, for purposes of regulating the elimination of $CO_2$. Another conceivable approach is the combined feed of oxygen into the first chamber and a gaseous anesthetic into the second chamber. By the same token, first artificial respiration can be carried out and subsequently, toxic substances—a possible cause of pulmonary failure—can be removed in the second chamber. This is done, for instance, by performing a dialysis of the blood flow.

In a practical manner, the device has means that allow fluids to be fed into and discharged from the system. These are, for instance, connectors or openings. In a special embodiment, the invention has a special flow guidance for oxygen and carbon dioxide that allows the mass transfer between the gas flow and the blood flow by the double, direct countercurrent principle. For this purpose, oxygen is carried in the interior of the semi-permeable hollow fiber membranes 330 and 340 (in each case, one membrane is shown by way of example) located in the chambers 310 and 320, and it fills them. This is possible because the integrated blood pump, which is fitted with a means that allows especially quick installation and removal, is in heat-conducting contact with the cylinder 250, via which heat is given off to the blood as it flows past by the cylinder 250, thus controlling the temperature. Additional temperature control is possible, but not necessary in especially preferred embodiments.

Therefore, in a special embodiment, the fiber material of the inner chamber 310 can be used for the oxygenation and especially for the removal of carbon dioxide. The removal of carbon dioxide is particularly important precisely in the case of patients with pulmonary disease. The elimination can be increased by higher gas flow rates. The magnitude of the flow rates is limited by the pressure conditions that prevail in the oxygenator (risk of embolism). Thanks to the arrangement according to the invention, more $CO_2$ can be exhaled in comparison to conventional oxygenators.

The integrated blood pump is provided with a means that allows the pump to be quickly replaced at any time, even during operation. In an exemplary embodiment, this means can be a clamping closure or a screw closure mechanism. In an especially preferred embodiment, the device according to the invention has a quick-release closure mechanism.

In a particularly practical embodiment, the quick-release closure mechanism has means to generate a recoil force, for example, an elastically deformable material or a spring.

In an especially preferred embodiment, the quick-release closure mechanism has a spring element. The spring element ensures that the drive aggregate is affixed in such a way that the motor with the magnetic coupling can be pressed against the rotor module and that the drive aggregate retains its position, even when the coupling is being released.

For latching purposes, the quick-release closure has means that allow a quick and secure insertion as well as rapid removal. For instance, the spring element accelerates the removal of the drive element.

In a special embodiment, the quick-release closure is a bayonet coupling. The spring element causes the bayonet coupling to pop out when the drive is unlatched, so that in emergency situations, the drive can be quickly removed, even during operation. This ensures the safety of the patient.

The blood flows through a blood inlet 160 into the oxygenator and is first carried by the integrated blood pump through the recess 290 in the innermost cylinder 250 into the chamber 310 between the cylinder 250 and the cylinder 260. Subsequently, the blood flows through the passages 300 in the cylinder 260 into the chamber 320, which is made up of the cylinder 260 and the cylinder 270, and from there, through the openings 280 in the cylinder 270 out of the system via the blood outlet 180. The chambers are almost completely filled with semi-permeable fiber material 330 and 340, so that the blood flows past the membranes and mass transport can take place through diffusion. Owing to the described special arrangement, the concentration gradient is raised and the mass transport or gas transfer is improved, which is very important especially for the miniaturized, compact embodiment of the oxygenation system.

The blood inlet and blood outlet of the oxygenation system can be configured coaxially, so that a double-lumen catheter can be connected directly, without an adapter. This has the advantage that overlapping in the tube system is avoided and the time needed until the oxygenation system is ready for use is shortened. This is a decisive advantage, particularly during critical situations.

Figure 6:
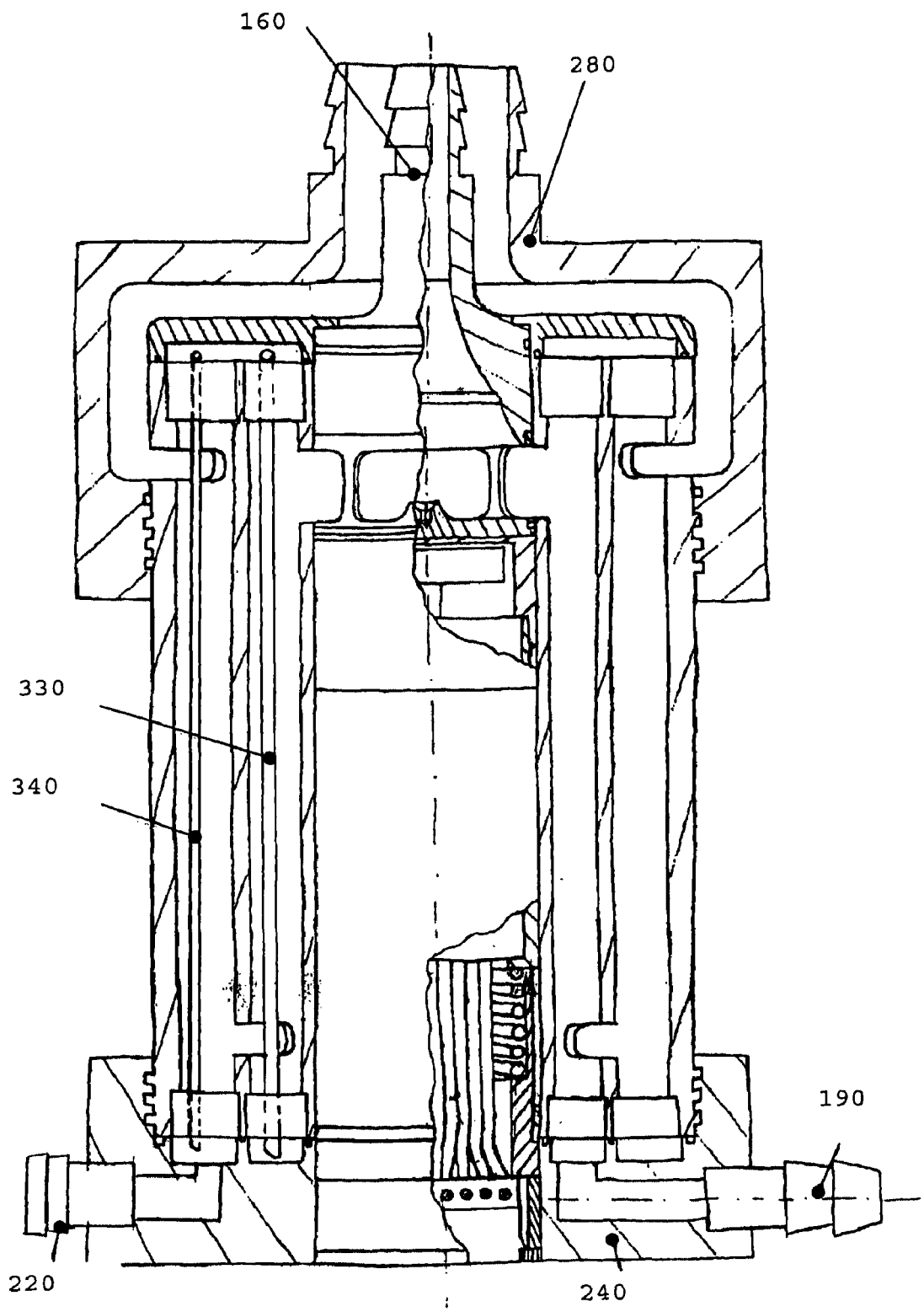
FIG. 6 is a cross-sectional view through a connection of an oxygenation system for connecting it to the patient by means of a double-lumen catheter.

FIG. 6 shows the coaxial connection for a double-lumen catheter. A specially designed blood cover 280 is arranged over the blood inlet 160. This cover 26 can optionally be used.

Figure 7:
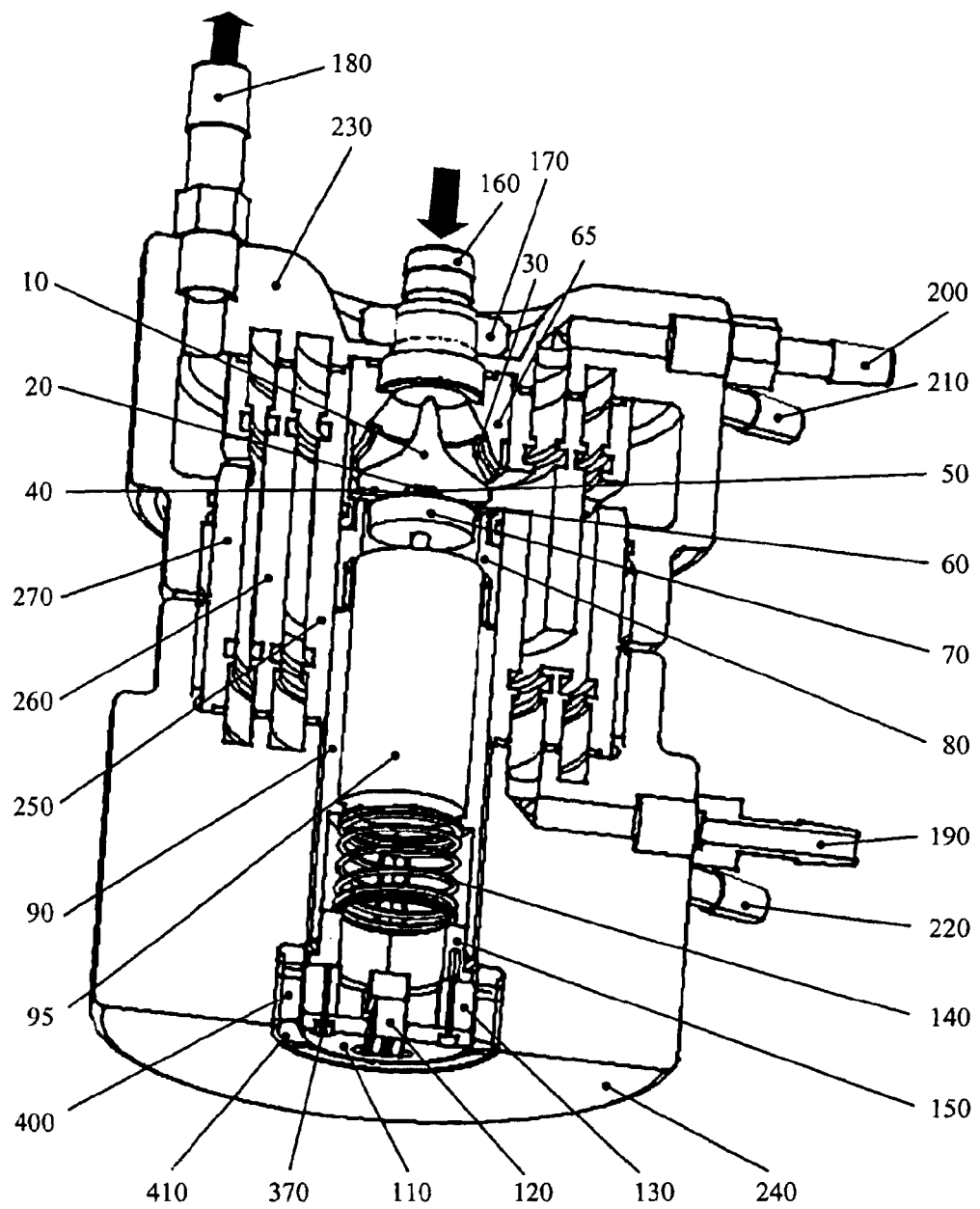
FIG. 7 is a perspective view of an alternative oxygenation system according to an exemplary embodiment of the present invention, showing the flow bearing of the blood pump and the quick-release closure.

FIG. 7 shows a section through another embodiment of the oxygenation system with an integrated blood pump. The system consists essentially of an oxygenator and a blood pump that is placed therein. The oxygenator consists of a membrane module made up of the cylinders 250, 260 and 270, as well as of the cover elements 230 and 240 on the ends. The blood pump is made up of the conveying modules 10-60 and drive modules 70-150.

For purposes of the assembly, the conveying module is inserted into the innermost cylinder 250 of the oxygenator. The conveying module is affixed by the shoulder formations on the opening of the cover 230 and by the nut 170.

The drive module has a quick-release closure that, in the present case, is configured as a bayonet coupling consisting of a connector holder 110 that affixes the connector 120, a ring element 130, a spring 140 and the return pins 150. When the unit is inserted into the oxygenation system, the coupling latches into the grooves 400 provided for this purpose in the cylinder element 410 that is connected to the cover 240. The spring presses the drive module against the rotor module, thus axially affixing the drive module. Depressing the button while turning the bayonet coupling causes it to unlatch once again. The spring causes the pushbutton 100, consisting of the elements 110-150, to pop out of the oxygenator housing, so that the drive unit can be easily and quickly removed from the oxygenator.

The impeller 10 is driven by the motor 90 by means of a magnetic coupling 40, 70. The support bearing 20, which absorbs the attractive forces from the magnetic coupling 40, 70, serves as the axial bearing of the impeller 10. The radial stabilization of the impeller 10 is effectuated contact-free by means of the fluid-mechanical bearing 30, which absorbs the tilting forces from the magnetic coupling 40, 70.

The drive module consists of a motor 95 with a magnetic coupling 70, an eight-pole cable and a connector 120. The motor with the magnetic coupling is completely surrounded by the motor housing 90 when the motor cover 80 is screwed on. The cable with the connector leads out of the housing. The connector is affixed in a multi-part device 110-150 by two screws 370 in such a way that a direct connection to the mating connector of the power supply is possible from the outside. The middle component of the three-part connector holder is a ring element 130 having two bores into which two alignment pins for the bayonet joint are inserted. The largest component of the connector holder 150 is provided with three hooks 150 on the side facing away from the connector. These hooks 150 engage with the slits 390 in the motor housing, thus holding the drive module together, but nevertheless allowing an axial movement relative to the motor housing 90. In the installed state, the spring 140 in the interior of the drive module ensures a play-free axial positioning of the motor housing 90 in the cylinder 250. When the bayonet joint is released, the spring pushes the connector and the holder out of the inner cylinder 250, while the other components of the drive module—at first unchanged—are held in the oxygenation unit by the attractive force of the magnetic coupling. The person operating the system can now grasp the connector holder and remove the drive module from the oxygenator. The motor has double protection against rotation due to the motor torque. The torque is directly absorbed by the motor housing into which the motor is clamped by the motor cover. The motor housing, in turn, is secured by the bayonet joint against turning, the torque is absorbed by the element pair consisting of the groove and pin.

The cover is made up of two parts and is arranged on the connector side. A bayonet groove 400 is provided in a separate cylinder 410, which considerably simplifies the production. The cylinder is connected to the cover 230 by means of a thread.

The flow guidance is effectuated by the fluid-mechanical bearing 30. The flow conveyed by the impeller 10 is then fed primarily into the flow channel between the first cylinder 250 and the second cylinder 260. After leaving the impeller 10, part of this flow is branched off into the ring channel between the impeller 10 and the surrounding housing. This reversely oriented flow brings about a radial stabilization of the impeller 10.

The conveying module consists of a conveying element 10, a bearing 20, 30, magnets 40, a universal ball joint 50, a base plate 60, an inlet 160 and a ring element 65. Like the drive module, this unit can be inserted into the membrane module and removed once again when necessary.

In the embodiments shown, the cover is screwed together to other parts. It is fundamentally possible to screw parts of the device to each other. This has the advantage of making it easier to disassemble.

It is likewise possible, however, to connect parts of the device to each other in any desired manner. Such possibilities include detachable connections, for instance, clamping connections or positive connections as well as non-detachable connections, for example, by producing injection-molded parts, by gluing or by welding.

Figure 8:
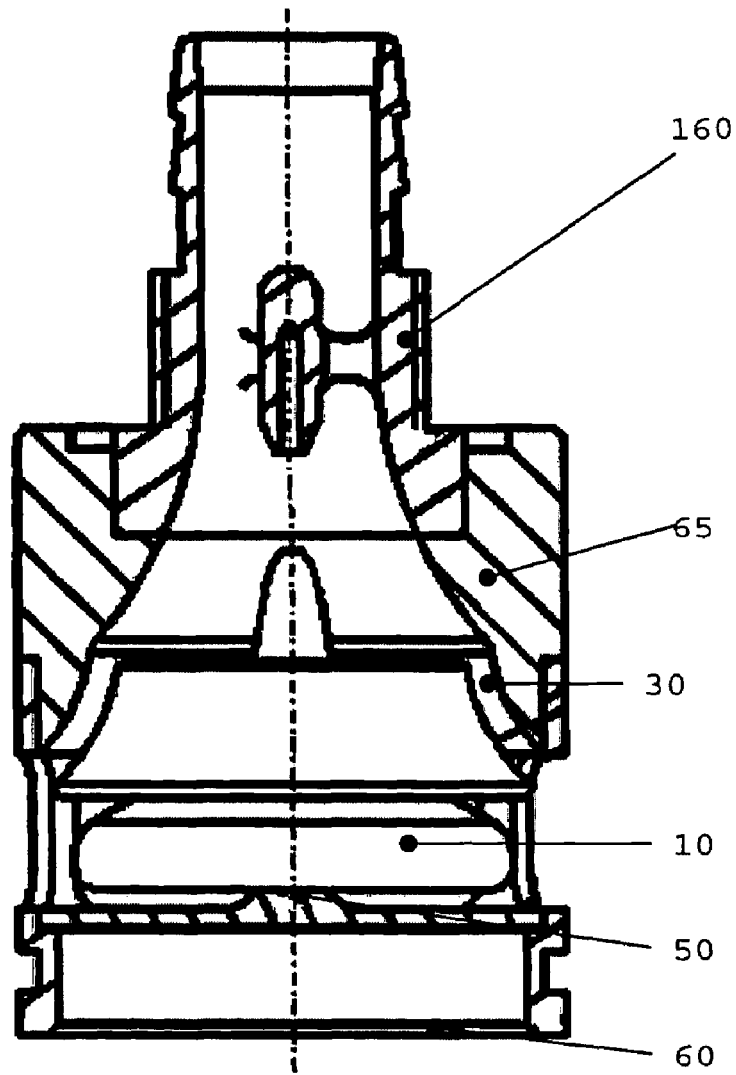
FIG. 8 is a cross-sectional view of a conveying module in accordance with an exemplary embodiment of the present invention.

FIG. 8 shows a conveying module consisting of a conveying element 10, a bearing 20, 30, magnets 40, a universal ball joint 50, a base plate 60, an inlet 160 and a ring element 65. Like the drive module, this unit can be inserted into the membrane module and removed once again when necessary.

Figure 9:
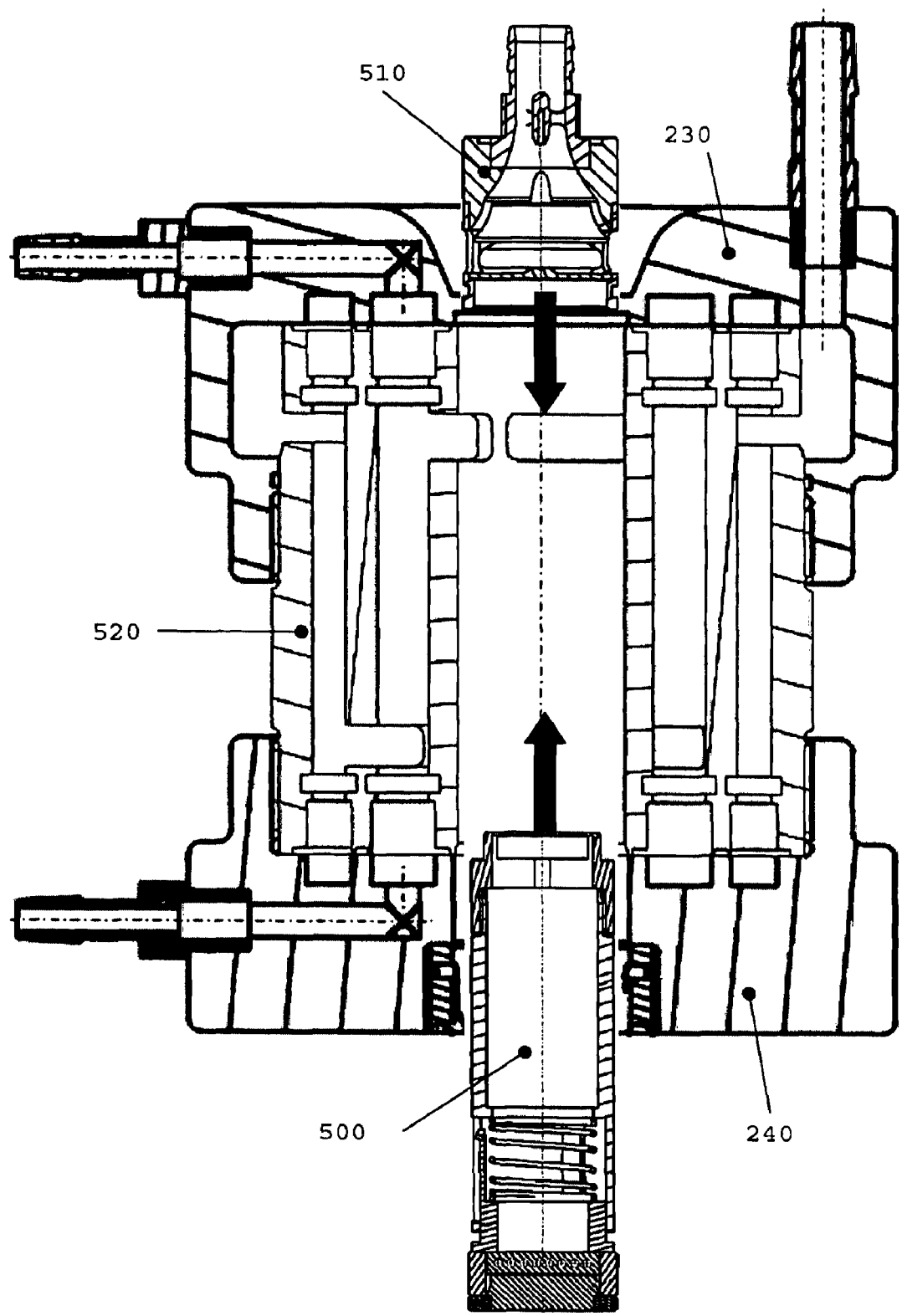
FIG. 9 is a cross-sectional view through the oxygenation system of FIG. 7, showing the module.

The arrows in FIG. 9 show in which preferred direction the drive module 500 and the conveying unit 510 are inserted into the oxygenator consisting of the membrane module 520 and the two covers 230, 240.

Figure 10:
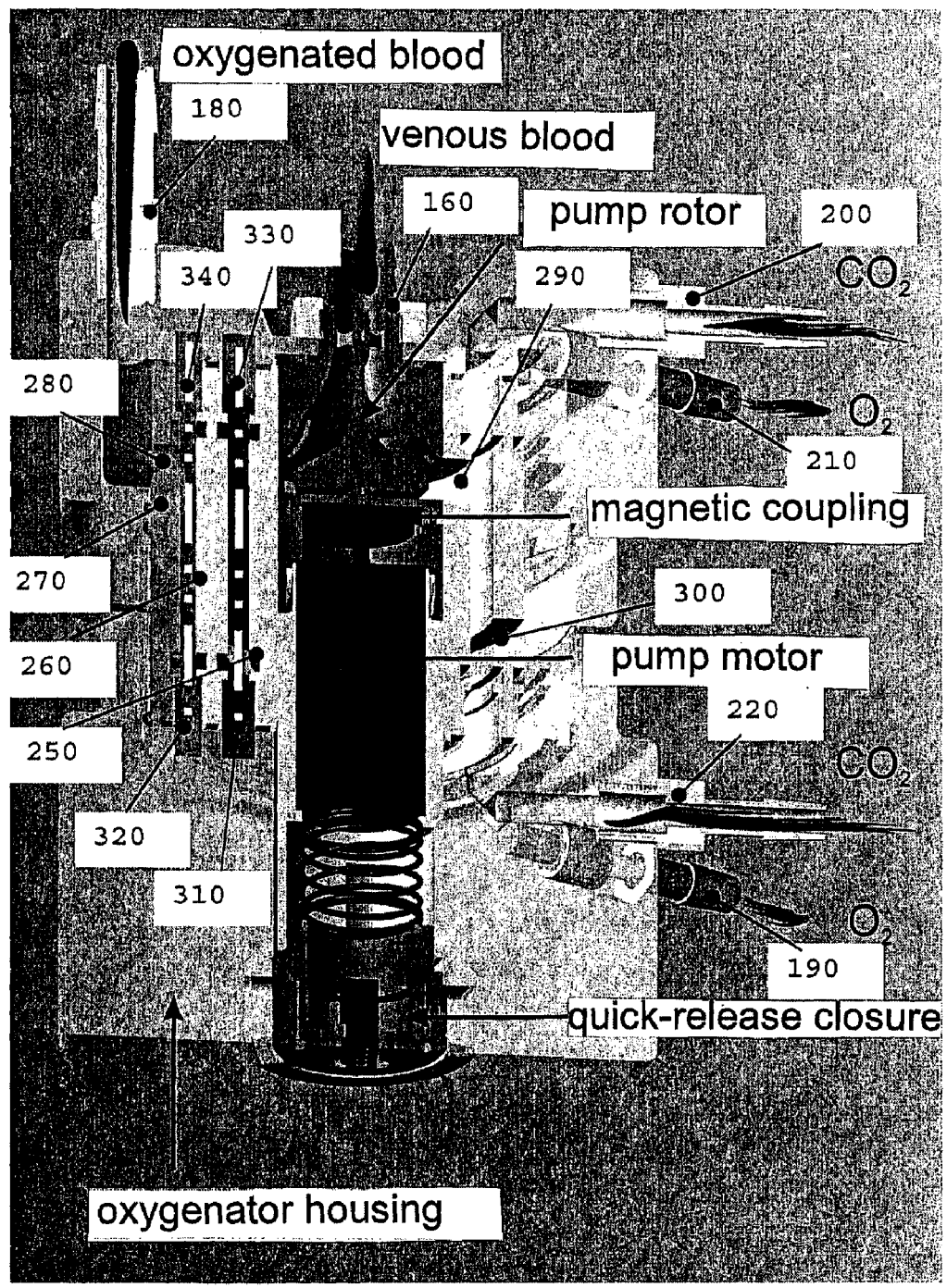
FIG. 10 is a schematic view that is useful in explaining the operation as well as the blood and gas flows in an exemplary embodiment of the present invention.

FIG. 10 illustrates a preferred course for the blood flow and the gas flow. Venous blood—drawn in by the blood pump—enters the oxygenation system at the inlet 160. The blood flow enriched with oxygen leaves the system at the outlet 180. Oxygen or ambient air flows into the system at the connections 190 and 210 and the gas flow enriched with carbon dioxide leaves the system at the openings 200 and 220.

The blood flow and the gas flow are carried twice in a countercurrent with respect to each other. The blood flows through the inlet 160 into the oxygenator. There, it flows—as indicated by the arrows—first through the opening 290 in the first cylinder 250 into the first chamber 310 that is closed at its ends by a suitable glued bond, where it then flows past the semi-permeable hollow fiber membranes 330. Subsequently, after the blood has passed the recesses 300 in the second cylinder 260, it flows in the opposite direction in the second chamber 320 that is likewise glued at its ends. The blood flows into the blood cover via the passages 280 in the third cylinder 270 and leaves the system through the blood outlet 180. The double countercurrent oxygenation is made possible in that oxygen first enters the system through the gas inlet 190 and subsequently flows into the chamber 310 through the membranes 330 that are arranged between the first cylinder 250 and the second cylinder 260. This gas flow leaves the oxygenation system through the outlet 200. A second gas flow 210 is concurrently carried through the membranes 340 into the chamber 320, between the second cylinder 260 and the third cylinder 270, and then flows out again through the second gas outlet 220.

An especially preferred embodiment of the device comprises technical features that are based on an extremely compact and modular structure and that make it possible to assist the lungs (and/or heart) by providing an adequate oxygen supply and by removing carbon dioxide. The oxygenation system according to the invention was developed with an eye towards ease of handling and re-usability. A blood pump consisting of a conveying module and a drive module is completely inserted into the system and affixed and locked in place by a quick-release closure. The motor unit transfers the torque onto the rotor contact-free by means of a magnetic coupling. The rotor of the pump is fluid-mechanically bearing-mounted, as a result of which it is particularly gentle on the blood and suitable for long-term use. Moreover, this type of bearing allows a modular structure of the system, so that the blood pump unit can be easily assembled and re-used. The blood temperature is controlled by the heat given off by the motor, so that it is possible to dispense with a heat exchanger. A double-lumen catheter can be connected to the special, coaxial connection for purposes of minimally invasive use.

An especially preferred embodiment has means that allow a modular structure of the system. Particularly for time-saving assembly, the rotor area is configured in such a way that the rotor is located in a housing that can be easily inserted into the oxygenation module for assembly purposes.

FIG. 9 illustrates an especially preferred embodiment of the procedure. Other conceivable embodiments are those with different types of rotors or bearings which, without changing the rest of the system, can be used as alternatives, depending on the given application.

Like the rotor cage, the drive aggregate can also be replaced. In particular, the drive aggregate can be replaced quickly during operation. This is made possible by a quick-release closure mechanism. Particularly in critical situations where there is a need for fast action, it must be ensured that a defective drive can be promptly replaced by a new one. The modular design here also allows the use of different drive aggregates. Thus, for instance, in a special embodiment, the drive can be a turbine that uses the gas flow from the oxygen tank as the drive and that is not dependent on the power supply or on a battery pack.

In contrast to the lower ball bearing (mechanical bearing), a contact-free fluid-bearing of the rotor is present in the inlet area of the blood pump and it stabilizes the impeller in the radial direction. The advantages of the contact-free radial bearing are, aside from the minimization of wear and tear, especially also the reduced risk of thrombocyte aggregation and damage to the blood. Furthermore, the manufacturing effort and thus also the production costs are lowered accordingly since the entire structure of the pump and oxygenation system is considerably simplified by such a bearing.

On the basis of the contact-free radial bearing, the pump can be installed in the oxygenator quickly and easily since the installation tolerances of the radial bearing can be selected to be very large. Moreover, the number of pump parts is reduced, which likewise contributes to lowering the manufacturing effort.

The blood pump is integrated into the housing in such a way that the outlet of the pump opens directly into the inlet of the gas-transfer means. Owing to this compact structure, the need for tube connections between the drive system and the oxygenator is avoided. This reduces the filling volume of the system.

The conveying module and the drive module including the magnetic coupling of the modularly structured integrated rotary blood pump can be easily inserted through the opening provided in the base cover for this purpose. The drive unit is securely locked in place and affixed by means of a quick-release closure mechanism. In a special embodiment, the quick-release closure can be a bayonet coupling. After use or in critical situations (e.g. failure of the pump), the safety mechanism can be quickly unlatched and the drive unit can be rapidly replaced. The re-usability of the durable blood pump unit saves resources and is environmentally very advantageous.

In a preferred embodiment, a heat exchanger can be dispensed with since the heat from the motor of the integrated blood pump automatically compensates for the heat loss of the blood flow that occurs via the oxygenator surface in the case of small and large blood flow rates so successfully and without the use of a control unit that the physiological body temperature is maintained in the blood. This further reduces the filling volume and the surface area of the oxygenator that comes into contact with the outside. The patient's risk of hemorrhaging as well as of systemic, inflammatory reactions and infections is thus diminished.

Figure 11:
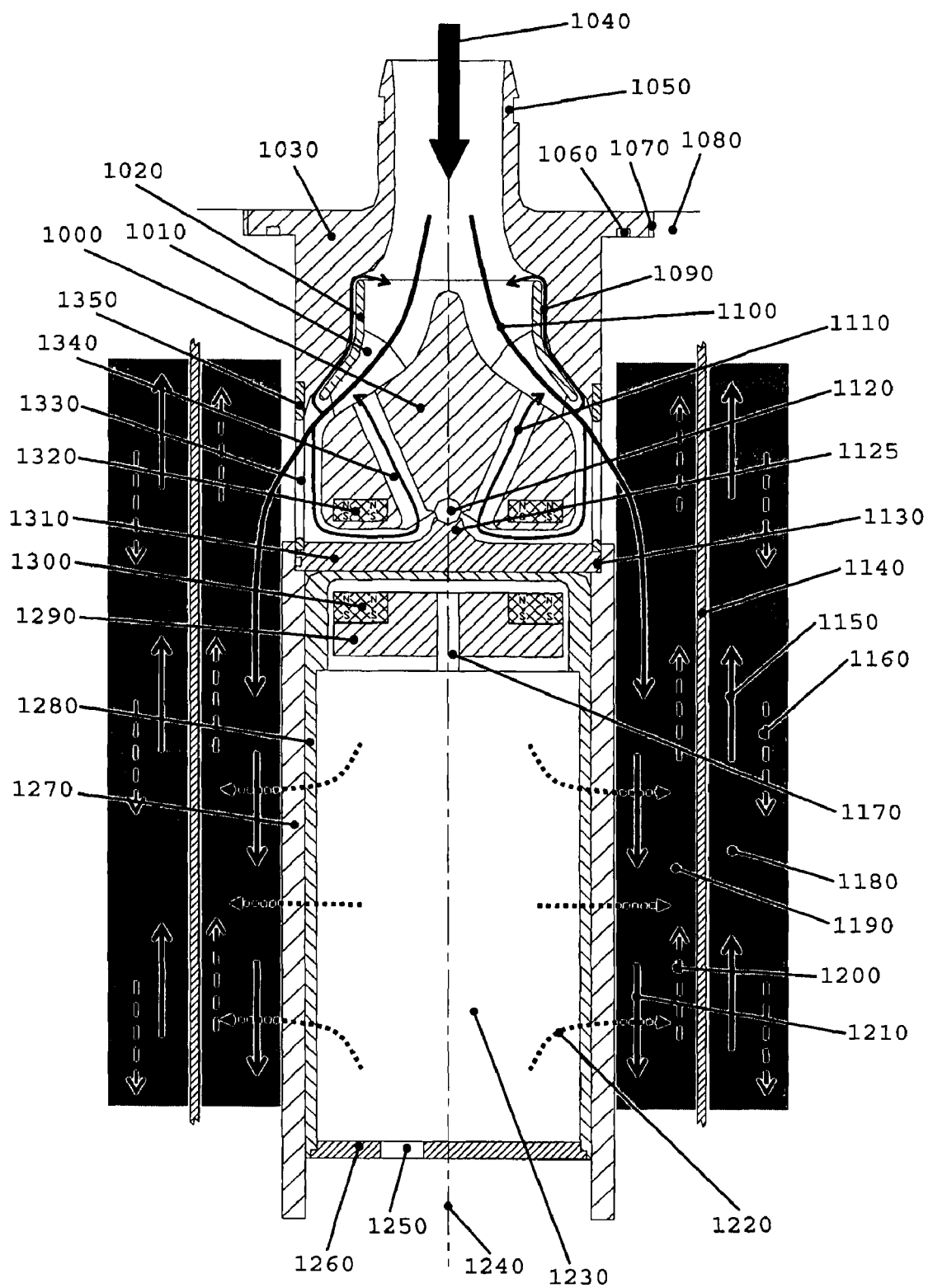
FIG. 11 is cross-sectional view of a pump unit of an oxygenator, including the flow guidance and the gas guidance; a drive using an integrated electric motor with a permanent-magnetic axial coupling.

FIG. 11 shows an oxygenator with an integrated blood pump 1000, 1010, 1020, 1030, 1050, 1070, 1310, 1350 and an integrated drive unit 1230, whereby the torque is transferred from the drive 1230 to the impeller contact-free by means of a permanent magnetic axial coupling 1300, 1320.

The blood flow 1040 is fed into the pump via the pump inlet 1050, after which it flows as a main flow 1100 through the blade area 1010 of the impeller 1000. Due to the pressure build-up in the pump, aside from the main flow 1100, additional secondary flows 1090, 1110 occur that are of crucial importance for the pump to operate in a way that the blood can tolerate. The higher pressure at the impeller outlet causes part of the main flow 1100 to be branched off at the impeller outlet as a flushing flow 1110 and to flow through the axial gap between the back of the impeller 1000 and the pump cover on the opposite side. Due to the pressure gradient, this flushing flow 1110 is oriented radially towards the inside and is also carried back to the front of the impeller via the flushing channels 1340 that have been machined in the impeller body 1000.

In this manner, the flow effectively flows through the back of the impeller, which is critical when it comes to thrombus deposits, thus keeping that area free of flow stagnation, and it also efficiently flushes and thus cools off the pivoting bearing 1120, 1125 of the impeller situated in this area. This ultimately results in a flow guidance at the back of the impeller that is gentle on the blood.

Another part of the main flow 1100 is likewise branched off as a leakage flow as a result of the pressure distribution in the impeller, from where it flows through the radial gap between the cover disk 1020 that is firmly joined to the impeller blades and/or to the other parts of the impeller as well as, optionally, to the pump housing 1030 on the opposite side.

In an especially preferred embodiment, this leakage flow 1090 is effectively employed to radially stabilize the impeller 1000, whereby the stabilization is due to the fluid forces that prevail in the gap. The mode of operation of this radial bearing is primarily based on a "Lomakin effect".

When the impeller 1000 is in a concentric position in the pump housing 1030, a constant static pressure prevails along the circumference in the bearing gap 1090. However, if the impeller is deflected in lateral directions, the bearing gap narrows on the deflected side and is enlarged accordingly on the diametrically opposite side of the gap. Since the pressure in the narrower gap area rises relative to the pressure in the diametrically opposite side owing to the different flow resistance, the result on the cover disk 1020 and thus on the impeller 1000 is a radial recovery force that moves the impeller 1000 back again to the concentric position in the pump housing 1030. Consequently, a radially effective bearing is present which, together with the pivoting bearing—that is to say, the ball track bearing—1120, 1125 creates a complete rotor bearing of the impeller 1000 in the pump housing 1030, without any mechanical contact occurring between these two components.

In this embodiment, the drive of the impeller is based on a permanent magnetic axial coupling 1300, 1320 that functions like a rotary face coupling. Due to the axially attractive magnetic forces between the drive magnets 1300 and the driven magnets 1320, the torques provided by the electric motor 1230 are transferred to the impeller 1000 contact-free. The drive magnets and the driven magnets each consist of an even number of reciprocally polarized permanent magnets (for example, NdFeB, SmCO, etc.). The presence of a load moment on the driven side causes the magnets 1300 on the drive side to continue to turn relative to the driven magnets 1320 until the magnetic air gap moment equals the load moment.

In this process, the axial attractive forces are absorbed by the pivoting bearing 1120, 1125, thus preventing the impeller 1000 from striking against the pump cover 1310. Since the impeller 1000, however, is mounted in the pivoting bearing 1120, 1125 unstably against lateral tilting in the pump housing 1030, there is a need for another radial bearing that constitutes the above-mentioned fluid bearing 1090 in accordance with the "Lomakin effect".

Figure 12:
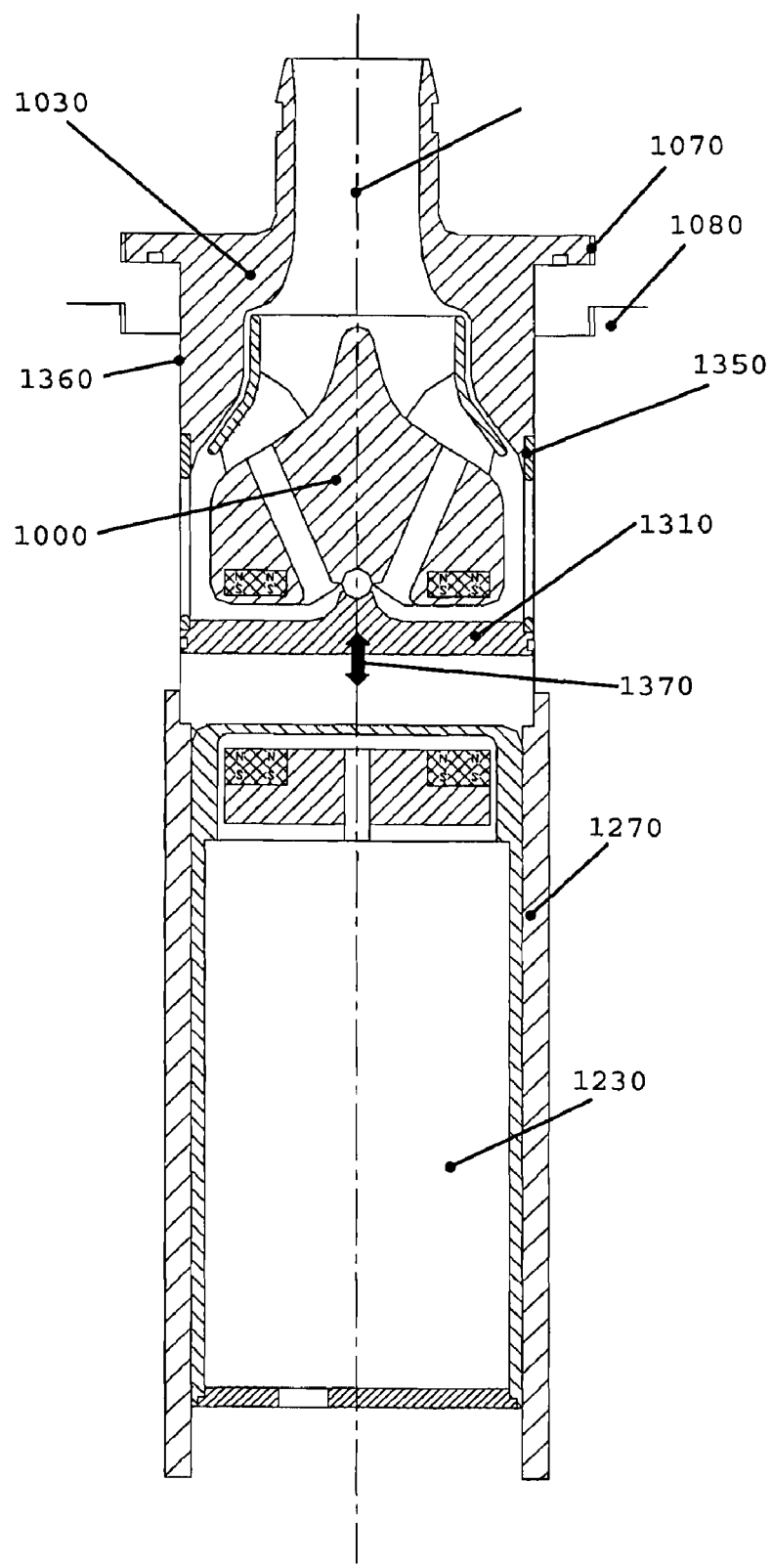
FIG. 12 is a cross-sectional view of an exemplary embodiment of the oxygenator according to FIG. 11, with an axially moveable pump unit.

FIG. 12 shows the oxygenator from FIG. 11 illustrating the simple installation and removal 1370 of the pump unit. As shown, for example, in FIG. 12, the installation and removal of the modular pump unit are made possible by a screw device 1070 situated between the pump housing 1030 and the adjacent stationary oxygenator element 1080.

This fact that the pump unit can be installed and removed offers the decisive advantage that, in case of technical complications (for instance, elevated bearing wear due to high operating output of the blood pump) or hematological complications in the pump area (for example, thrombus deposits in the blood pump) during clinical use, particularly during prolonged use (e.g. ECMO), the oxygenator can continue to be used by simply replacing the pump unit, so that the patient does not have to undergo another oxygenation treatment and this could mean that there is no need for an additional surgical procedure and so the ECMO treatment can be carried out in a manner that is altogether easier on the patient.

Figure 13:
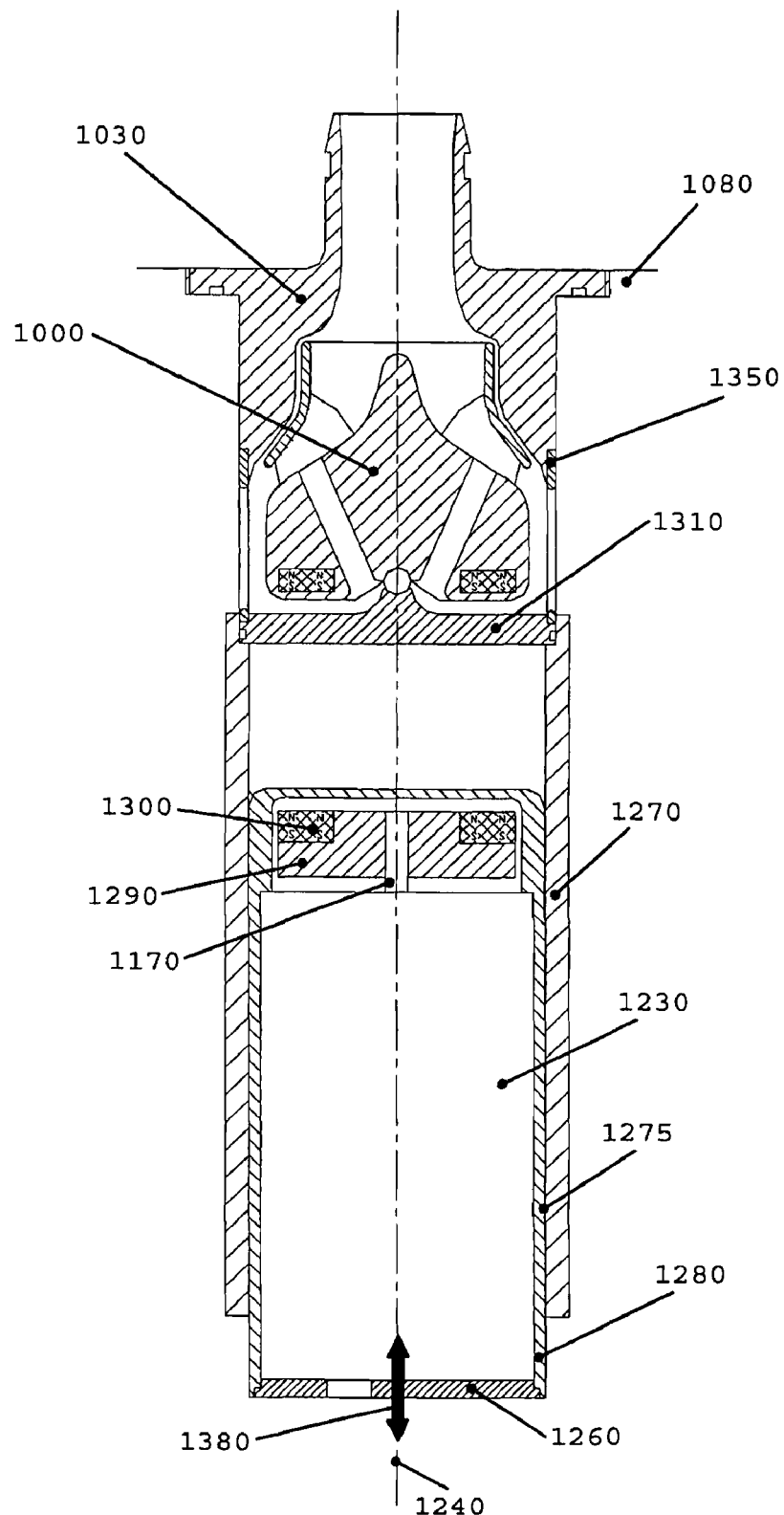
FIG. 13 is a cross-sectional view of an exemplary embodiment of the oxygenator according to FIG. 11, with an axially moveable drive unit.

FIG. 13 shows the oxygenator from FIG. 11 illustrating the simple installation and removal 1370 of the pump unit. The installation and removal of the modular drive unit are assisted by a suitable quick-release closure. The fact that the pump unit can be installed and removed offers the decisive advantage that the drive module 1170, 1230, 1280, 1290, 1300, whose production is technically demanding, can always be used for additional deployments, even if the oxygenator module was used once, as a result of which the oxygenator can be used in a more cost-effective manner. An essential special feature of this integrated drive concept is that Joule's heat loss given off into the environment can be effectively utilized to control the temperature of the blood in the oxygenation module. An additional heat exchanger, as is currently needed with blood oxygenation systems, can be circumvented in this embodiment of the oxygenator, so that the oxygenation system is more compact overall and correspondingly easier to operate.

Figure 14:
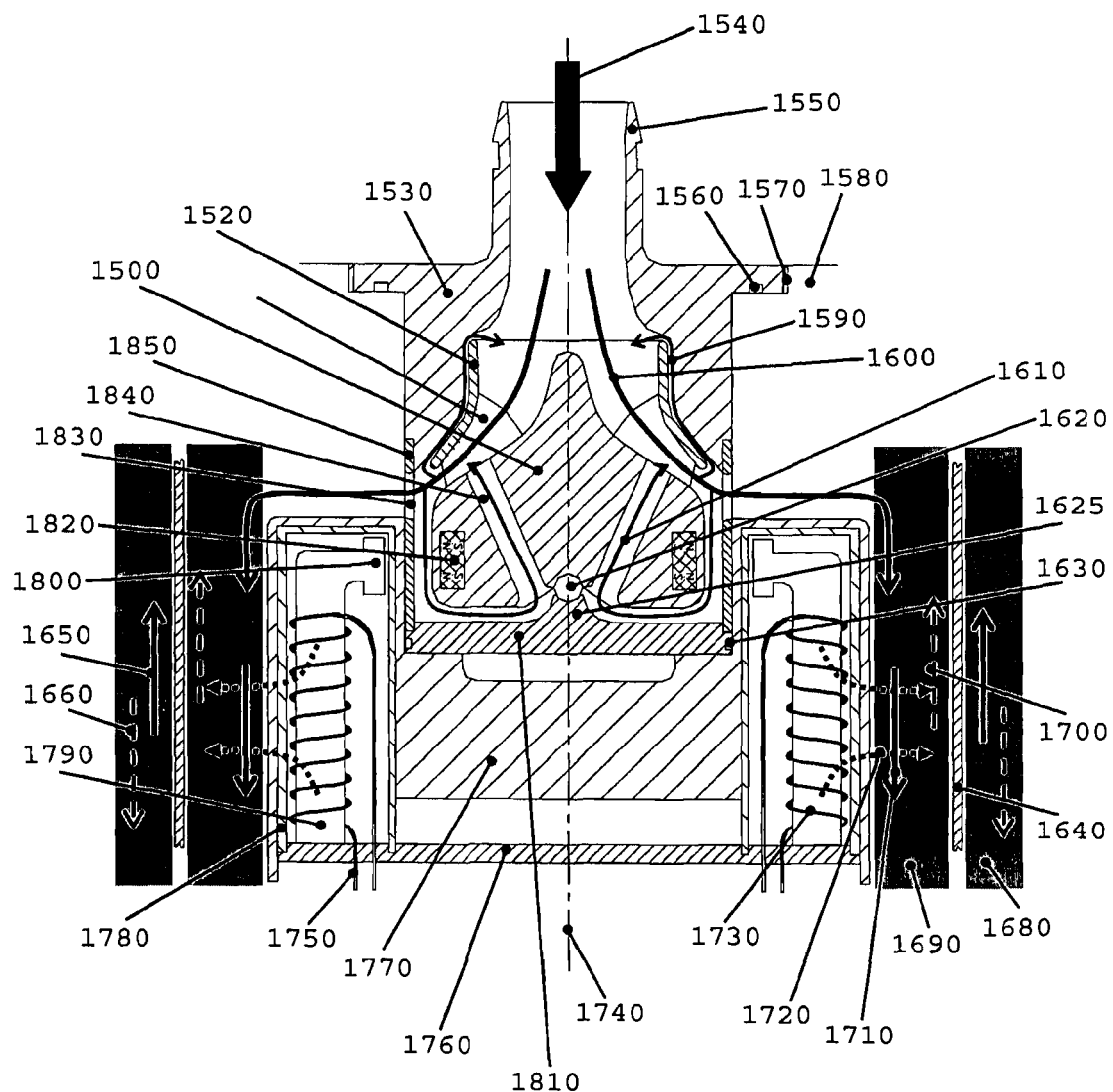
FIG. 14 is a cross-sectional view of a pump unit of the oxygenator in accordance with an exemplary embodiment, including the flow guidance and the gas guidance; drive using an integrated electric motor with an electromagnetic radial coupling.

FIG. 14 shows an oxygenator with an integrated blood pump 1500, 1510, 1520, 1530, 1550, 1570, 1810, 1850 and an integrated drive unit 1230, 1730, 1790, 1800, whereby the torques are transferred from the drive 1800 to the impeller 1500 contact-free by means of an electromagnetic radial coupling 1800, 1820. The structure and the mode of operation of this magnetic radial coupling is comparable to that of the axial magnetic coupling shown in FIG. 11, with the essential difference that here, the driven magnets 1820 are not magnetized in the axial direction but rather in the radial direction. Here, as well, an even number of permanent magnet segments face each other on the drive side and on the driven side, causing a contact-free torque transmission that becomes effective when a load moment is applied under rotation.

The essential advantage of an oxygenator according to the configuration in FIG. 14 lies in the fact that the magnetic radial coupling likewise provides a stable axial bearing which, in particular, reduces the mechanical loads onto the pivoting bearing.

The use of Joule's heat to control the temperature of the blood and of the gases in the oxygenator likewise brings about the advantages already mentioned in conjunction with FIG. 11.

Figure 15:
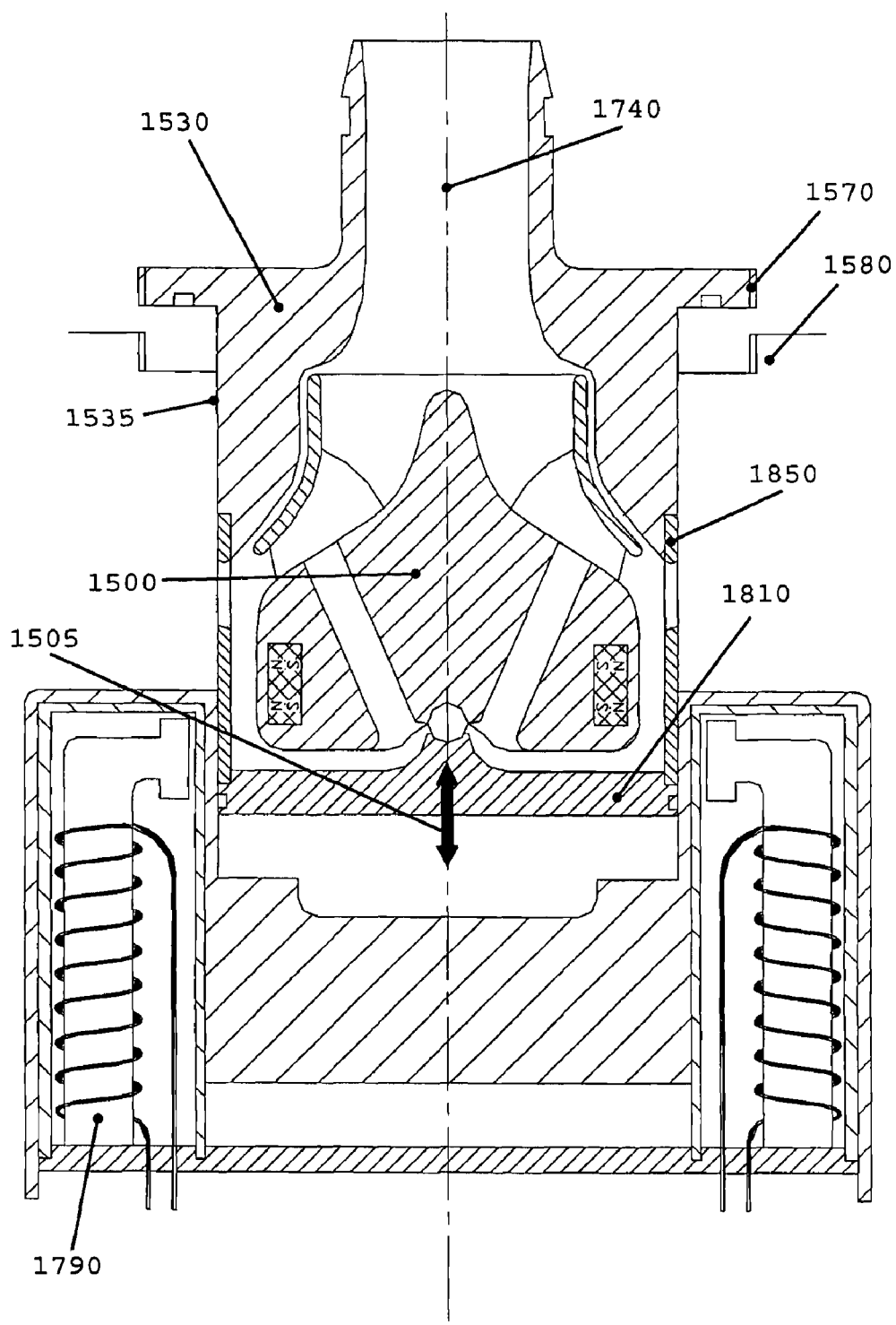
FIG. 15 is a cross-sectional view of an exemplary embodiment of the oxygenator according to FIG. 14, with an axially moveable pump unit.
Figure 16:
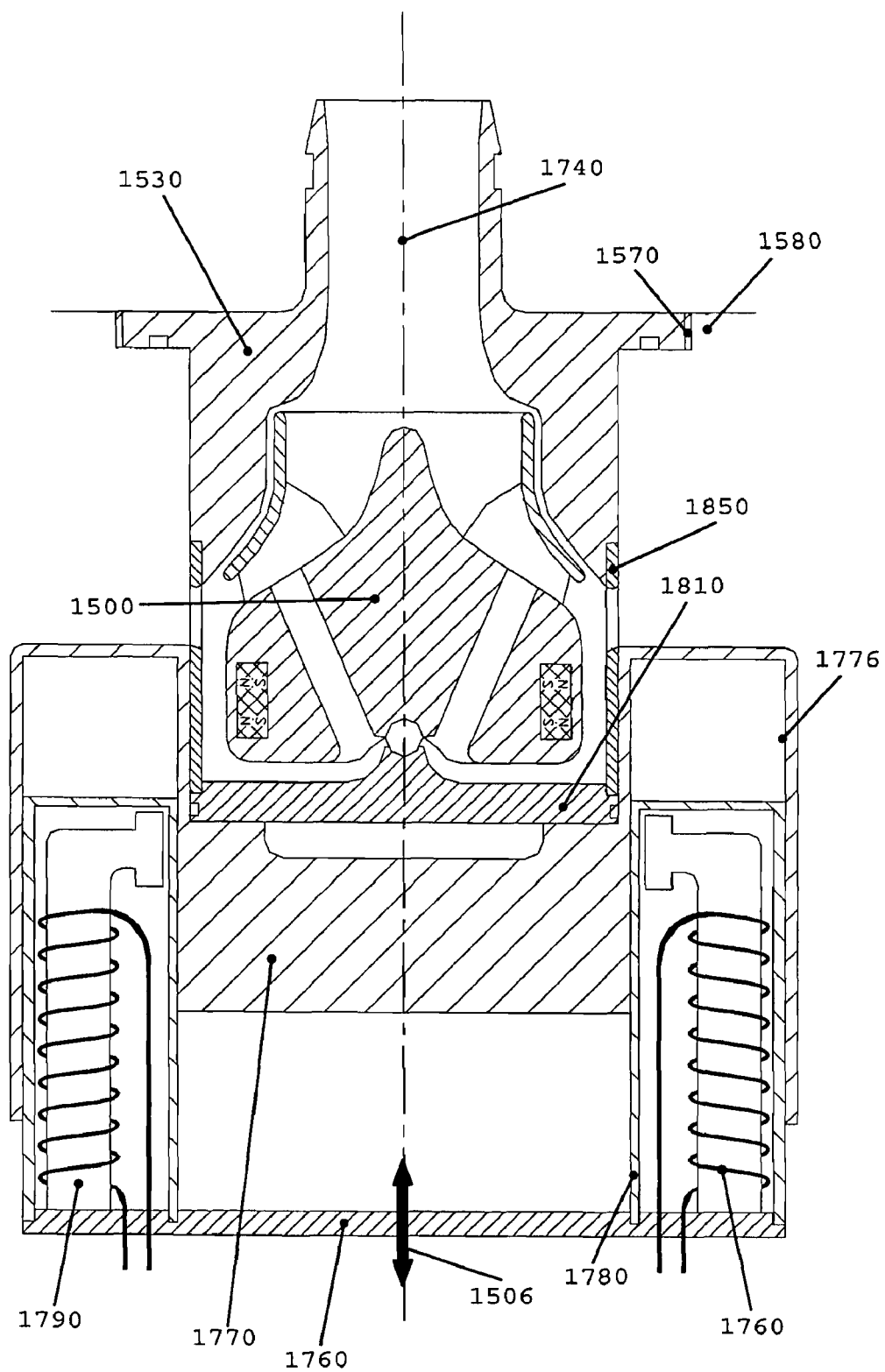
FIG. 16 is a cross-sectional view of an exemplary embodiment of the oxygenator according to FIG. 14, with an axially moveable drive unit.

Also in the configuration of the oxygenator according to FIG. 14, a simple installation and removal of the pump unit and of the drive unit are ensured, as is shown by way of an example in FIGS. 15 and 16.

Figure 17:
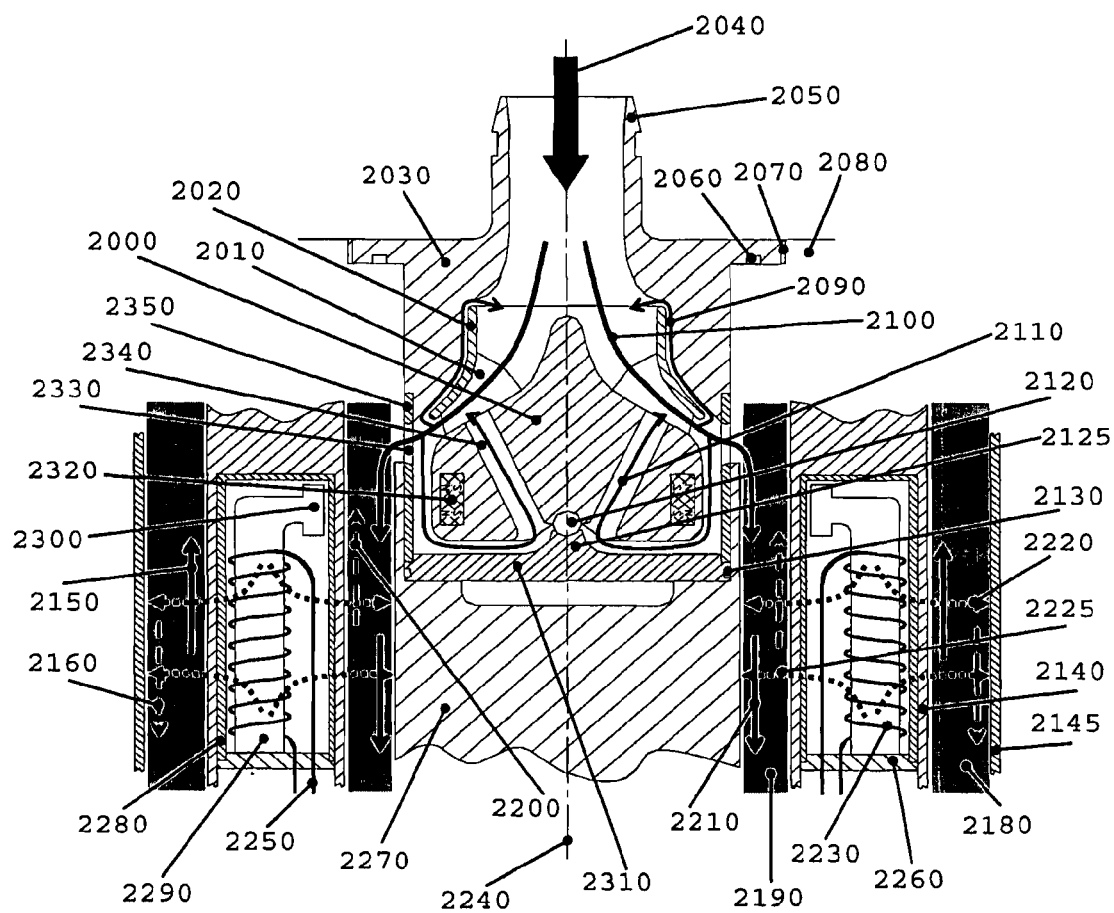
FIG. 17 is a cross-sectional view of a pump unit of an exemplary oxygenator, including the flow guidance and the gas guidance; a drive using an integrated electric motor with an electromagnetic radial coupling; the stator unit of the drive is surrounded by oxygenator fibers on both sides.
Figure 18:
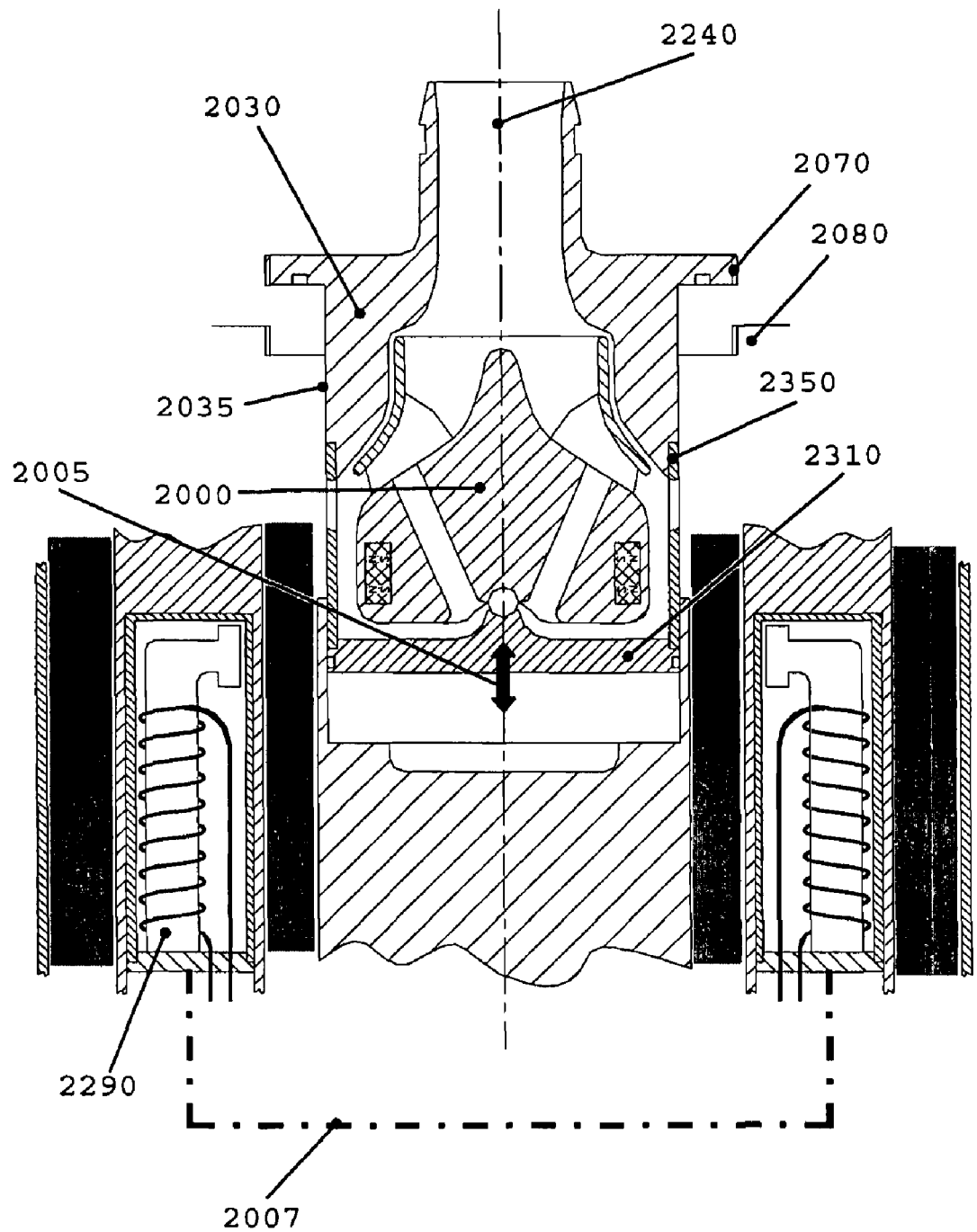
FIG. 18 is a cross-sectional view of an exemplary embodiment of the oxygenator according to FIG. 17, with an axially moveable pump unit.
Figure 19:
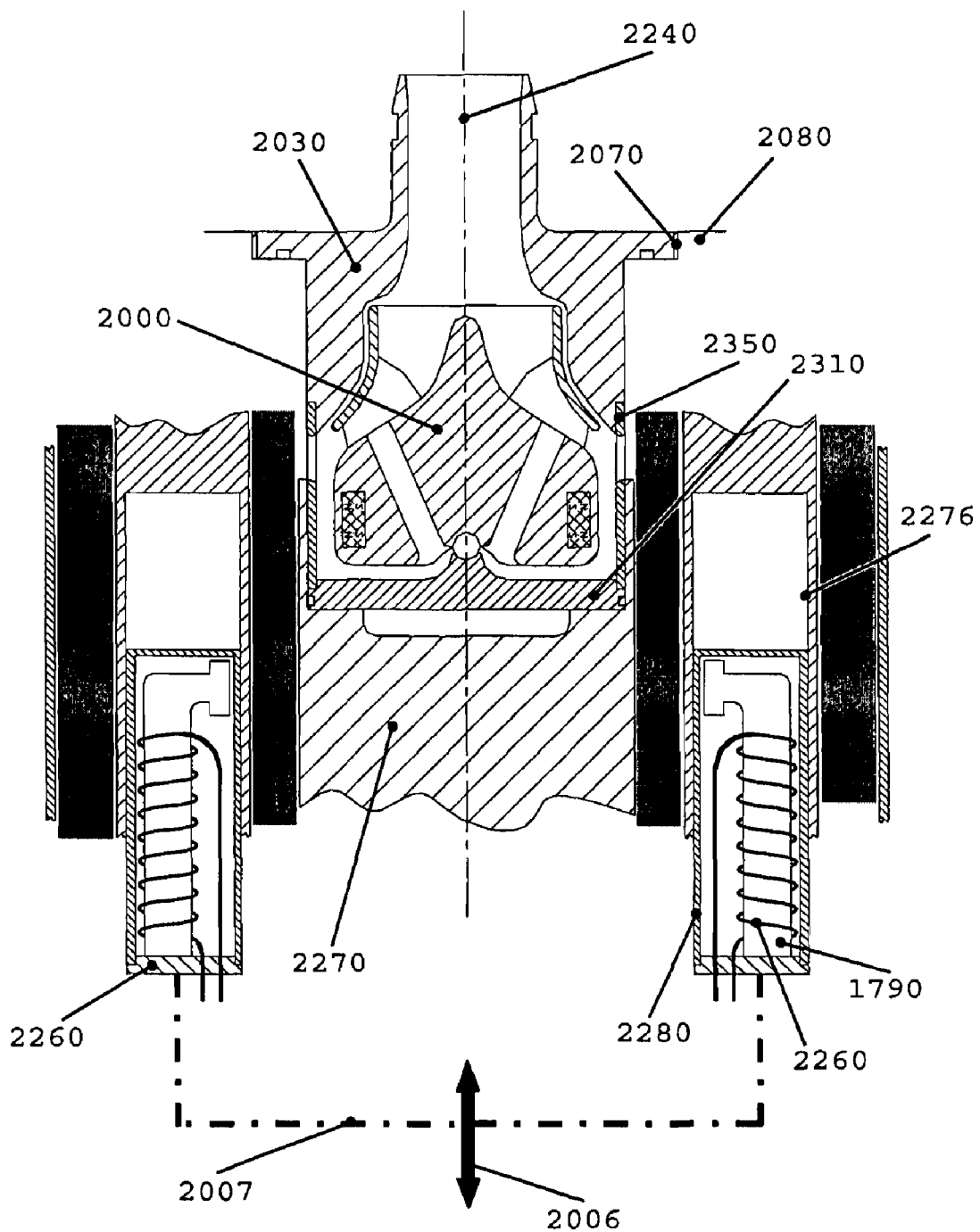
FIG. 19 is a cross-sectional view of an exemplary embodiment of the oxygenator according to FIG. 17, with an axially moveable drive unit.

FIG. 17 shows an oxygenator with an integrated blood pump 2000, 2010, 2020, 2030, 2050, 2070, 2310, 2350 and an integrated drive unit 2230, 2260, 2280, 2290, 2300, whereby the torques are transferred from the drive 2300 to the impeller 1500 contact-free by means of an electromagnetic radial coupling 1800, 1820. The structure and the mode of operation of this magnetic radial coupling are comparable to that of the radial magnetic coupling shown in FIG. 14, with the essential difference that here, the stator unit 2230, 2290, 2300 of the drive does not give off Joule's heat generated in it to the oxygenation module 2180, 2190 only on one side, as shown in FIGS. 11 and 14, but rather on both sides. This is made possible by the concentric placement of the stator unit 2230, 2290, 2300 between two oxygenation modules 2180, 2190 whereby, in the case of oxygenation module 2190 situated radially on the inside, said stator unit absorbs Joule's heat via its cylindrical outer circumferential surface and, in the case of the oxygenation module 2180 situated radially on the outside, said stator unit absorbs Joule's heat via its cylindrical inner circumferential surface.

As a result, the essential advantage exists that the temperature control of the blood that is exposed to cooling in the extracorporeal circulation (without an additional heat exchanger) can be implemented much more efficiently.

The other advantages of such a radial magnetic coupling, particularly in terms of its bearing and stabilization function, can be gleaned from the elaborations pertaining to FIG. 14.

The modular structure of the oxygenation system, consisting of disposable parts (fibers, membranes, etc.) as well as of replaceable or re-usable modules (pump unit, drive unit), exists in the case of the embodiment of the oxygenator according to FIG. 17 as well. Therefore, the advantages of a modular structure for an oxygenator according to FIG. 17 can be directly gleaned from those pertaining to FIGS. 11 and 14.

Especially preferred embodiments of the device are suitable, for instance, for patients with acute pulmonary failure (acute respiratory distress syndrome—ARDS). In such cases, extracorporeal membrane oxygenation (ECMO) provides suitable assistance. With this therapy, roller pumps or centrifugal pumps are employed to convey blood through a membrane oxygenator. The blood is enriched with oxygen and carbon dioxide is depleted through semi-permeable membranes. Heat exchangers are used to control the temperature of the blood. These devices are operated exclusively stationarily.

Thanks to the ease of handling as well as the sturdy and compact design, the device according to the invention is also easy to transport and can already be employed directly, for instance, at the site of an accident. This increases the chances of survival of patients with very severe pulmonary damage and gives the lungs the necessary rest to heal.

Due to the low filling volume and the reduced surface area of the high filling volume that comes into contact with the outside, the device according to the invention reduces risks such as infections, damage to the red blood cells and thrombocyte aggregation as well as the risk of hemorrhaging since it allows the administration of the requisite anticoagulant heparin. Thanks to the modular structure of preferred embodiments, which clearly separates the re-usable blood pump unit from the disposable unit that comes into contact with the blood, namely, the membrane module, the invention can be considered to be effective and efficient, both in terms of its production and its operation.

LIST OF REFERENCE NUMERALS 10 impeller
20 support bearing
30 fluid-mechanical bearing
40 permanent magnets
50 universal ball joint
60 base plate of the conveying module
65 ring element
70 magnetic coupling
80 motor cover
90 motor housing
95 drive aggregate
100 pushbutton
110 connector holder
120 connector
130 ring element with bores
140 spring element
150 connector holder
155 return hooks
160 blood inlet
170 screw
180 blood outlet
190 gas inlet
200 gas outlet
210 gas inlet
220 gas outlet
230 cover
240 cover (base)
250 cylinder
260 cylinder
270 cylinder
280 openings
290 openings
300 openings
310 chamber
320 chamber
330 fiber material
340 fiber material
350 glued bond
360 glued bond
370 screws
380 alignment pins
390 slits
400 bayonet groove
410 cylinder element
500 drive module
510 conveying module
520 membrane module
1000 impeller
1010 impeller blades
1020 cover disk
1030 pump housing
1040 inflow to the blood pump or to the oxygenator
1050 pump inlet
1060 gasket (for example, O-ring gasket)
1070 thread
1080 stationary oxygenator element
1090 leakage flow or fluid bearing
1100 main flow
1110 flushing flow
1120 bearing ball (pivoting bearing)
1125 universal ball joint
1130 gasket (for example, O-ring gasket)
1140 separation element between the oxygenator fibers or membranes
1150 blood flow in the outside fiber bundle
1160 gas flow in the outside fiber bundle
1170 motor shaft
1180 outside fiber bundle
1190 inside fiber bundle
1200 gas flow in the inside fiber bundle
1210 blood flow in the inside fiber bundle
1220 heat flow from the electric motor to the oxygenator
1230 electric motor
1240 rotary axis
1250 exit of the motor cable
1260 motor cover
1270 hollow cylinder as a separation between the motor and the oxygenator
1275 sliding surface between the drive unit and the adjacent stationary oxygenator element
1280 motor housing
1290 pole shoe of the magnetic coupling
1300 drive magnets
1310 pump cover
1320 driven magnets
1330 flow channel in the outlet device leading to the blood pump
1340 flushing channel
1350 cage-type outlet device
1360 sliding surface between the pump unit and the adjacent stationary oxygenator element
1370 direction of movement during installation and removal of the pump unit
1380 direction of movement during installation and removal of the drive unit
1500 impeller
1505 direction of movement during installation and removal of the pump unit
1506 direction of movement during installation and removal of the drive unit
1510 impeller blades
1520 cover disk
1530 pump housing
1535 sliding surface between the pump unit and the adjacent stationary oxygenator element
1540 inflow to the blood pump or to the oxygenator
1550 pump inlet
1560 gasket (for example, O-ring gasket)
1570 thread
1580 stationary oxygenator element
1590 leakage flow or fluid bearing
1600 main flow
1610 flushing flow
1620 bearing ball (pivoting bearing)
1625 universal ball joint
1630 gasket (for example, O-ring gasket)
1640 separation element between the oxygenator fibers or membranes
1650 blood flow in the outside fiber bundle
1660 gas flow in the outside fiber bundle
1680 outside fiber bundle
1690 inside fiber bundle
1700 gas flow in the inside fiber bundle
1710 blood flow in the inside fiber bundle
1720 heat flow from the electric motor to the oxygenator
1730 windings (stator coils) of the electromagnetic drive
1740 rotary axis
1750 exit of the motor cable
1760 motor cover 1770 stationary device for separating the drive unit from the oxygenator
1776 sliding surface between the drive unit and the adjacent stationary oxygenator element
1780 motor housing
1790 stator magnet of the electromagnetic drive
1800 stator magnet opposite from driven magnets
1810 pump cover
1820 driven magnets
1830 flow channel in the outlet device leading to the blood pump
1840 flushing channel
1850 cage-type outlet device
2000 impeller
2005 direction of movement during installation and removal of the pump unit
2006 direction of movement during installation and removal of the drive unit
2007 device in the oxygenator that has the axially movable drive as a single part
2010 impeller blades
2020 cover disk
2030 pump housing
2035 sliding surface between the pump unit and the adjacent stationary oxygenator element
2040 inflow to the blood pump or to the oxygenator
2050 pump inlet
2060 gasket (for example, O-ring gasket)
2070 thread
2080 stationary oxygenator element
2090 leakage flow or fluid bearing
2100 main flow
2110 flushing flow
2120 bearing ball (pivoting bearing)
2125 universal ball joint
2130 gasket (for example, O-ring gasket)
2140 separation element between the oxygenator fibers or oxygenator membranes
2145 delimitation of the oxygenator fibers and oxygenator membranes
2150 blood flow in the outside fiber bundle
2160 gas flow in the outside fiber bundle
2180 outside fiber bundle
2190 inside fiber bundle
2200 gas flow in the inside fiber bundle
2210 blood flow in the inside fiber bundle
2220 heat flow from the electric motor to the outside oxygenator bundle
2225 heat flow from the electric motor to the inside oxygenator bundle
2230 windings (stator coils) of the electromagnetic drive
2240 rotary axis
2250 exit of the motor cable
2260 motor cover
2270 stationary device for separating the drive unit from the oxygenator
2276 sliding surface between the drive unit and the adjacent stationary oxygenator element
2280 motor housing
2290 stator magnet of the electromagnetic drive
2300 stator magnet opposite from driven magnets
2310 pump cover
2320 driven magnets
2330 flow channel in the outlet device leading to the blood pump
2340 flushing channel
2350 cage-type outlet device

What is claimed is:

1. A device for enriching and/or depleting substances in a liquid, comprising:
 a membrane module that consists essentially of concentric elements and that has a separation element in which the substance to be enriched and/or depleted is carried, and whereby the liquid is carried outside of the separation element;
 a drive module that encompasses a drive unit for driving a conveying element that conveys the liquid, the drive unit having a radial magnetic coupling for a central impeller located on the inside;
 a conveying module for conveying the liquid through the device, housing the conveying element, whereby the drive module is adapted to be inserted into and removed from the membrane module with a liquid-tight closure;
 an oxygenator having an outside fiber bundle and an inside fiber bundle; and
 an electromagnetic drive unit disposed between the outside fiber bundle and the inside fiber bundle.

2. The device according to claim 1, wherein the drive unit is adapted to warm up the outside fiber bundle as well as the inside fiber bundle.

3. The device according to claim 1, wherein the separation element has hollow fibers made of semi-permeable material for purposes of enriching and/or depleting the liquid, whereby the substance to be depleted and/or enriched is carried in the fibers and the liquid is carried outside of the fibers.

4. The device according to claim 1, wherein the conveying module for conveying the liquid is arranged in an axial extension of the drive module.

5. The device according to claim 1, wherein the conveying element and a housing that surrounds the conveying element are arranged so that they can be separated from each other.

6. The device according to claim 1, wherein the conveying element is replaceable if the conveying element is sealed so as to be liquid-tight relative to a feed line for the liquid and/or to a discharge line for the liquid.

7. The device according to claim 1, wherein the drive unit is arranged in such a way as to be at least partially surrounded by the liquid.

8. The device according to claim 7, wherein the drive unit is separated from the liquid by at least one partition.

9. The device according to claim 1, wherein the drive unit has a quick-release closure on at least one end.

10. The device according to claim 9, wherein the quick-release closure is positioned at one end of the drive unit.

11. The device according to claim 9, wherein the quick-release closure comprises a bayonet coupling.

12. The device according to claim 9, wherein the quick-release closure comprises is a screw closure.

13. The device according to claim 9, wherein the quick-release closure comprises is a clamp-type closure.

14. The device according to claim 9, wherein the quick-release closure comprises a magnetic closure.

15. The device according to claim 1, wherein a shock-absorbing element is arranged between the drive unit and a rotor unit.

16. The device according to claim 1, wherein the membrane module has at least two elements arranged concentrically with respect to each other, whereby the separation element is arranged between a first element and a second element.

17. The device according to claim 16, wherein the membrane module has at least three elements arranged concentrically with respect to each other, whereby the separation element is arranged between the first element and the second element, and whereby another separation element is arranged between the second element and the third element.

18. The device according to claim 16, wherein spaces between the elements are sealed at the ends so as to be liquid-tight.

19. The device according to claim 16, wherein the conveying module is adapted to be placed inside the interior of an innermost of three elements and can be inserted into and it removed from it.

20. The device according to claim 16, wherein an innermost of three elements of the membrane module has a cover with a quick-release closure on the side opposite from the conveying module.

21. The device according to claim 1, wherein a radial outer diameter of the conveying module is smaller than the radius of the interior of the innermost element.

22. The device according to claim 21, wherein the conveying module is adapted to be inserted into the interior of the innermost element during the assembly of the device.

23. The device according to claim 1, wherein a cap is adapted to be placed onto one end of a cylinder, the cap having a feed line and a discharge line arranged coaxially to each other for feeding and discharging the liquid.

24. The device according to claim 1, wherein hollow fibers placed between a first cylinder and a second cylinder and between the second and a third cylinder, each of the first, second and third cylinders have a substance feed line and a substance discharge line.

25. The device according to claim 24, wherein a gas feed line of the hollow fibers placed between the first and the second cylinders is placed at one end of the first and second cylinders and a gas feed line of the fibers placed between the second and the third cylinders is placed at an opposite end of the second and third cylinders relative to the first and second cylinders.

26. The device according to claim 1, wherein a transmission of force from the drive unit to the conveying element is contact-free.

27. The device according to claim 26, wherein the transmission of force from the drive unit to the conveying element is affected by a magnetic coupling.

28. The device according to claim 1, wherein the device has an essentially cylindrical receptacle for accommodating the drive unit.

29. The device according to claim 1, wherein the drive unit produces heat during operation.

30. The device according to claim 1, wherein the drive unit comprises a motor.

31. The device according to claim 1, wherein the drive unit is in heat-conducting contact with a cylindrical receptacle.

32. The device according to claim 31, wherein the liquid is carried along the outside of the cylindrical receptacle.

33. The device according to claim 1, wherein the conveying element has a fluid-mechanical bearing in the radial direction.

34. The device according to claim 33, wherein the fluid-mechanical bearing is effectuated by a secondary flow that runs counter to a main conveying flow in a space between the conveying element and the surrounding housing.

35. The device according to claim 33, wherein the conveying element is mounted in a solid axial bearing in the side facing the drive module.

36. The device according to claim 1, wherein the device comprises at least two drive modules.

37. The device according to claim 36, wherein the at least two drive modules are connected in a series connection.

38. The device according to claim 36, wherein the at least two drive modules are connected in a parallel connection.

39. A device for enriching and/or depleting substances in a liquid, comprising
 membrane module means that consists essentially of concentric elements and that has a separation element in which the substance to be enriched and/or depleted is carried, and whereby the liquid is carried outside of the separation element;
 drive module means that encompasses a drive unit for driving a conveying element that conveys the liquid, the drive unit having a radial magnetic coupling for a central impeller located on the inside;
 conveying module means for conveying the liquid through the device, housing the conveying element, whereby the drive module is adapted to be inserted into and removed from the membrane module with a liquid-tight closure;
 oxygenator means having an outside fiber bundle and an inside fiber bundle; and
 electromagnetic drive means disposed between the outside fiber bundle and the inside fiber bundle.

40. A method of enriching and/or depleting substances in a liquid, comprising
 employing a membrane module that consists essentially of concentric elements and that has a separation element in which the substance to be enriched and/or depleted is carried, and whereby the liquid is carried outside of the separation element;
 employing a drive module that encompasses a drive unit for driving a conveying element that conveys the liquid, the drive unit having a radial magnetic coupling for a central impeller located on the inside;
 employing a conveying module for conveying the liquid, the conveying module housing the conveying element, whereby the drive module is adapted to be inserted into and removed from the membrane module with a liquid-tight closure;
 employing an oxygenator having an outside fiber bundle and an inside fiber bundle; and
 employing an electromagnetic drive unit disposed between the outside fiber bundle and the inside fiber bundle conveying liquid through the membrane module.

* * * * *